(12) United States Patent
Nguyen et al.

(10) Patent No.: US 9,561,247 B2
(45) Date of Patent: Feb. 7, 2017

(54) METHODS AND COMPOSITIONS FOR WOUND TREATMENT

(71) Applicant: Halscion, Inc., Suwanee, GA (US)

(72) Inventors: Tien Nguyen, Daly City, CA (US); Kathleen Prudhomme, Atlanta, GA (US); Ronald Yamamoto, San Francisco, CA (US); Adam G. Lowe, Snellville, GA (US); Andrew Michael Green, Cumming, GA (US)

(73) Assignee: TIF Management, LLC, Duluth, GA (US)

( * ) Notice: Subject to any disclaimer, the term of this patent is extended or adjusted under 35 U.S.C. 154(b) by 0 days.

(21) Appl. No.: 13/666,718

(22) Filed: Nov. 1, 2012

(65) Prior Publication Data

US 2013/0108700 A1    May 2, 2013

Related U.S. Application Data

(60) Provisional application No. 61/554,870, filed on Nov. 2, 2011.

(51) Int. Cl.
| | | |
|---|---|---|
| A61K 31/721 | (2006.01) | |
| A61K 38/01 | (2006.01) | |
| A61K 9/00 | (2006.01) | |
| A61L 26/00 | (2006.01) | |
| A61K 47/42 | (2006.01) | |

(52) U.S. Cl.
CPC ........... *A61K 31/721* (2013.01); *A61K 9/0014* (2013.01); *A61K 9/0021* (2013.01); *A61K 9/0024* (2013.01); *A61K 38/014* (2013.01); *A61L 26/008* (2013.01); *A61L 26/0023* (2013.01); *A61L 26/0038* (2013.01); *A61L 26/0052* (2013.01); *A61K 47/42* (2013.01); *A61L 2400/06* (2013.01)

(58) Field of Classification Search
None
See application file for complete search history.

(56) References Cited

U.S. PATENT DOCUMENTS

| | | |
|---|---|---|
| 4,446,316 A | 5/1984 | Chazov et al. |
| 4,520,821 A | 6/1985 | Schmidt et al. |
| 4,614,794 A | 9/1986 | Easton et al. |
| 4,618,490 A | 10/1986 | De Marco |
| 4,772,468 A | 9/1988 | Pfirrmann |
| 4,863,856 A | 9/1989 | Dean, Jr. et al. |
| 4,883,487 A | 11/1989 | Yoshizato et al. |
| 4,895,724 A | 1/1990 | Cardinal et al. |
| 4,902,295 A | 2/1990 | Walthall et al. |
| 4,950,483 A | 8/1990 | Ksander et al. |
| 4,957,902 A | 9/1990 | Grinnell |
| 4,965,203 A * | 10/1990 | Silbering et al. ............ 435/188 |
| 4,997,753 A | 3/1991 | Dean, Jr. et al. |
| 5,099,012 A | 3/1992 | Wu et al. |
| 5,100,783 A | 3/1992 | Dean, Jr. et al. |
| 5,192,743 A | 3/1993 | Hsu et al. |
| 5,263,983 A | 11/1993 | Yoshizato et al. |
| 5,290,558 A | 3/1994 | O'Leary et al. |
| 5,303,718 A | 4/1994 | Krajicek |
| 5,350,583 A | 9/1994 | Yoshizato et al. |
| 5,376,375 A | 12/1994 | Rhee et al. |
| 5,457,093 A | 10/1995 | Cini et al. |
| 5,470,911 A | 11/1995 | Rhee et al. |
| 5,484,601 A | 1/1996 | O'Leary et al. |
| 5,514,379 A | 5/1996 | Weissleder et al. |
| 5,569,468 A | 10/1996 | Modi |
| 5,591,709 A | 1/1997 | Lindenbaum |
| 5,605,938 A | 2/1997 | Roufa et al. |
| 5,614,205 A | 3/1997 | Usala |
| 5,645,591 A | 7/1997 | Kuberasampath et al. |
| 5,705,178 A * | 1/1998 | Roufa et al. ............ 514/59 |
| 5,705,485 A | 1/1998 | Cini et al. |
| 5,707,877 A | 1/1998 | Siiman et al. |
| 5,716,404 A | 2/1998 | Vacanti et al. |
| 5,718,012 A | 2/1998 | Cavallaro |
| 5,733,337 A | 3/1998 | Carr, Jr. et al. |
| 5,756,715 A | 5/1998 | Monte et al. |
| 5,783,214 A | 7/1998 | Royer |
| 5,800,541 A | 9/1998 | Rhee et al. |
| 5,824,331 A | 10/1998 | Usala |

(Continued)

FOREIGN PATENT DOCUMENTS

| | | |
|---|---|---|
| EP | 0 213 908 | 3/1987 |
| WO | WO 92/19195 | 11/1992 |

(Continued)

OTHER PUBLICATIONS

"Gel Foam MSDS", "Material Safety Data Sheet", 2012, accessed from: http://www.btps.ca/files/PDF/MSDS/Gelatin_Powder.pdf, pp. 1-5.*

Mahindru, S.N., "Food Additives", 2008, APH Publishing Corporation, pp. 217.*

Anderson, V. and Jones, R., "The Influence of Gelatin on the Mechanism of Phase Separation of a Biopolymer Mixture," *Polymer*, 2001, pp. 9601-9610, vol. 42, Elsevier Science Ltd.

Antonov, Y. and Zubova, O., "Phase State of Aqueous Gelatin-Polysaccharide (1)-Polysaccharide (2) Systems," *International Journal of Biological Macromolecules*, 2001, pp. 67-71, vol. 29, Elsevier Science Ltd., B.V.

(Continued)

*Primary Examiner* — Michael G Hartley
*Assistant Examiner* — Lance Rider
(74) *Attorney, Agent, or Firm* — Womble Carlyle Sandridge & Rice, LLP

(57) ABSTRACT

The present invention provides compositions and methods useful in the treatment of wounds, particularly in reducing or preventing scar formation, particularly hypertrophic scar or keloid formation. The invention thus further provides methods of treatment, including methods useful in hypertrophic scar or keloid revision as well as prophylactic, scar inhibiting methods.

17 Claims, 3 Drawing Sheets

(56) References Cited

U.S. PATENT DOCUMENTS

| | | | |
|---|---|---|---|
| 5,830,492 | A | 11/1998 | Usala |
| 5,834,005 | A | 11/1998 | Usala |
| 5,866,165 | A | 2/1999 | Liu et al. |
| 5,922,339 | A | 7/1999 | Usala |
| 5,972,385 | A | 10/1999 | Liu et al. |
| 5,993,844 | A | 11/1999 | Abraham et al. |
| 6,011,008 | A | 1/2000 | Domb et al. |
| 6,077,916 | A | 6/2000 | Laurencin et al. |
| 6,083,930 | A | 7/2000 | Roufa et al. |
| 6,132,759 | A | 10/2000 | Schacht et al. |
| 6,165,488 | A | 12/2000 | Tardy et al. |
| 6,197,330 | B1 | 3/2001 | Rees et al. |
| 6,231,881 | B1 | 5/2001 | Usala et al. |
| 6,261,587 | B1 | 7/2001 | Usala |
| 6,264,992 | B1 | 7/2001 | Voytik-Harbin et al. |
| 6,303,585 | B1 | 10/2001 | Spiro et al. |
| 6,352,707 | B1 | 3/2002 | Usala |
| 6,391,052 | B2 | 5/2002 | Buirge et al. |
| 6,458,386 | B1 | 10/2002 | Schacht et al. |
| 6,833,408 | B2 | 12/2004 | Sehl et al. |
| 7,666,413 | B2 | 2/2010 | Liu et al. |
| 7,695,736 | B2 | 4/2010 | Kararli et al. |
| 7,799,767 | B2 | 9/2010 | Lamberti et al. |
| 8,664,202 | B2 * | 3/2014 | Lamberti ............... A61L 27/26 514/17.2 |
| 9,066,991 | B2 | 6/2015 | Preiss-Bloom et al. |
| 2002/0019516 | A1 | 2/2002 | Noff et al. |
| 2002/0049281 | A1 | 4/2002 | Zhao et al. |
| 2002/0169201 | A1 | 11/2002 | Falchuk |
| 2002/0176893 | A1 | 11/2002 | Wironen et al. |
| 2002/0192263 | A1 | 12/2002 | Merboth et al. |
| 2003/0032098 | A1 | 2/2003 | Young et al. |
| 2003/0147935 | A1 | 8/2003 | Binette et al. |
| 2003/0220245 | A1 | 11/2003 | Hubbell et al. |
| 2004/0091462 | A1 | 5/2004 | Lin et al. |
| 2004/0138128 | A1 | 7/2004 | Lee et al. |
| 2005/0118230 | A1 | 6/2005 | Hill et al. |
| 2005/0176620 | A1 | 8/2005 | Prestwich et al. |
| 2006/0079599 | A1 * | 4/2006 | Arthur ............... A61L 24/0031 523/118 |
| 2009/0123520 | A1 * | 5/2009 | Harris ............... A61K 9/0021 424/425 |
| 2009/0130756 | A1 | 5/2009 | Klann et al. |
| 2011/0290693 | A1 * | 12/2011 | Harris ....................... 206/438 |
| 2012/0238937 | A1 | 9/2012 | Dean et al. |
| 2012/0270810 | A1 * | 10/2012 | Preiss-Bloom et al. ..... 514/21.2 |

FOREIGN PATENT DOCUMENTS

| | | |
|---|---|---|
| WO | WO 95/14037 | 5/1995 |
| WO | WO 97/41899 | 11/1997 |
| WO | WO 98/15299 | 4/1998 |
| WO | WO 00/02596 | 1/2000 |
| WO | WO 00/02600 | 1/2000 |
| WO | WO 00/56251 | 9/2000 |
| WO | WO 01/74411 | 10/2001 |

OTHER PUBLICATIONS

Arnold, P., et al., "Evaluation of Resorbable Barriers for Preventing Surgical Adhesions," *Fertility and Sterility*, 2000, pp. 157-161, vol. 73(1), Elsevier Science Inc.

Aso, Y., et al., "Thermally Controlled Protein Release From Gelatin-Dextran Hydrogels," *Radiation Physics and Chemistry*, 1999, pp. 179-183, vol. 55, Elsevier Science Ltd.

Barker, H., et al. "Formaldehyde as a Pre-Treatment of Dermal Collagen Heterografts," *Biochimica et Biophysica Acta*, 1980, pp. 589-597, vol. 632.

Boyan, B.D. et al., "Role of Material Surfaces in Regulating Bone and Cartilage Cell Response," *Biomaterials*, 1996, pp. 137-146, vol. 17.

Boyce, S.T. and Hansborough, J.F., Biologic Attachment, Growth, and Differentiation of Cultured Human Epidermal Keratinocytes on a Graftable Collagen and chondroitin-6-sulfate substrate, *Surgery*, 1988, pp. 421-431, vol. 103.

Bubnis, W.A. and Ofner C.M. III, "The Determination of ε-Amino Groups in Soluble and Poorly Soluble Proteinaceous Materials by a Spectrophotometric Method Using Trinitrobezenesulfonic Acid," *Anal. Biochem.*, 1992, pp. 129-133, vol. 207.

Butler, C., et al., "Regeneration of Neomucosa Using Cell-Seeded Collagen-GAG Matrices in Athymic Mice," *Annals of Plastic Surgery*, 2002, pp. 298-304, vol. 48, Lippincott Williams & Wilkins, Inc.

Choi, Y., et al., "Study on Gelatin-Containing Artificial Skin: I. Preparation and Characteristics of Novel Gelatin-Alginate Sponge," *Biomaterials*, 1999, pp. 409-417, vol. 20, Elsevier Science Ltd.

Choi, Y., et al., "Studies on Gelatin-Containing Artificial Skin: II. Preparation and Characterization of Cross-Linked Gelatin-Hyaluronate Sponge," *J. Biomed. Mater. Res. (Appl. Biomater.)* 1999, pp. 631-639, vol. 48, John Wiley & Sons, Inc.

Crescenzi, V., et al., "New Gelatin-Based Hydrogels Via Enzymatic Networking," *Biomacromolecules*, 2002, pp. 1384-1391, vol. 3, American Chemical Society.

De Kruif, C. and Tuinier, R., "Polysaccharide Protein Interactions," *Food Hydrocolloids*, 2001, pp. 555-563, vol. 15, Elsevier Science Ltd.

Ding, P., et al., "Interfacial Tension in Phase-Separated Gelatin/Dextran Aqueous Mixtures," *Journal of Colloid and Interface Science*, 2002, pp. 367-376, vol. 253, Elsevier Science USA.

Doukas, J., et al., "Delivery of FGF Genes to Wound Repair Cells Enhances Arteriogenesis and Myogenesis in Skeletal Muscle," *Molecular Therapy*, 2002, pp. 517-527, vol. 5(5), The American Society of Gene Therapy.

Edelman, M. and Van Der Linden, E., "Compatability of Gelatin and Dextran in Aqueous Solution," *Biomacromolecules*, 2001, pp. 1148-1154, vol. 2(4), American Chemical Society.

Edwards, G., et aL, "In vivo Evaluation of a Collagenous Membrane as an Absorbable Adhesion Barrier," *Journal of Biomedical Materials Research*, 1997, pp. 291-297, vol. 34, John Wiley & Sons, Inc.

Einerson, N., et al., "Synthesis and Physiochemical Analysis of Gelatin-Based Hydrogels for Drug Carrier Matrices," *Biomaterials*, 2002, pp. 509-523, vol. 24, Elsevier Science Ltd.

Freyman, T., et al., "Fibroblast Contraction of a Collagen-GAG Matrix," *Biomaterials*, 2001, pp. 2883-2891, vol. 22.

Freyman, T., et al., "Micromechanics of Fibroblast Contraction of a Collagen-GAG Matrix," *Experimental Cell Research*, 2001, pp. 140-153, vol. 269, Academic Press.

Friess, W., et al., "Insoluble Collagen Matrices for Prolonged Delivery of Proteins," *Pharm Dev. Technol.*, 1996, pp. 185-193, vol. 1(2).

Hansbrough, J.F., et al., "Burn Wound Closure with Cultured Autologous Keratinocytes and Fibroblasts Attached to a Collagen-Glycoasminoglycan Substrate," *JAMA*, 1989, pp. 2125-2130, vol. 262.

Holmes, T., "Novel Peptide-Based Biomaterial Scaffolds for Tissue Engineering," *TRENDS in Biotechnology*, 2002, pp. 16-21, vol. 20 (1), Elsevier Science, Ltd.

Hong, S., et al., "Study on Gelatin-Containing Artificial Skin IV: A Comparative Study on the Effect of Antibiotic and EGF on Cell Proliferation During Epidermal Healing," *Biomaterials*, 2001, pp. 2777-2783, vol. 22, Elsevier Science Ltd., United Kingdom.

Jansson, K., et al., "A Biodegradable Bovine Collagen Membrane as a Dermal Template for Human in vivo Wound Healing," *Scand. J. Plast. Reconstr. Hand Surg.*, 2001, pp. 369-375, vol. 35.

Kam, L., et al., "Selective Adhesion of Astrocytes to Surfaces Modified with Immobilized Peptides," *Biomaterials*, 2002, pp. 511-515, vol. 23, Elsevier Science Ltd.

Kao, W. and Lee, D., "In vivo Modulation of Host Response and Macrophage Behavior by Polymer Networks Grafted with Fibronectin-Derived Biomimetic Oligopeptides: the Role RGD and PHSRN Domains," *Biomaterials*, 2001, pp. 2901-2909, vol. 22, Elsevier Science Ltd.

(56) References Cited

OTHER PUBLICATIONS

Kao, W., et al., "Preparation of Heterodifunctional Polyethyleneglycols: Network Formation, Characterization, and Cell Culture Analysis," *J. Biomater. Sci. Polymer Edn*, 2001, pp. 599-611, vol. 12.

Kawai, K., et al., "Accelerated Tissue Regeneration through Incorporation of Basic Fibroblast Growth Factor-Impregnated Gelatin Microspheres into Artificial Dermis," *Biomaterials*, 2000, pp. 489-499, vol. 21, Elsevier Science Ltd.

Kosmala, J., et al., "Preparation of Interpenetrating Networks of Gelatin and Dextran as Degradable Biomaterials," *Biomaterials*, 2000, pp. 2019-2023, vol. 21, Elsevier Science Ltd.

Lebaron, R.G., et al., "Extracellular Matrix Cell Adhesion Peptides: Functional Applications in Orthopedic Materials," *Tissue Eng.*, 2000, pp. 85-103, vol. 6(2).

Lii, C., et al., "Carboxymethyl Cellulose-Gelatin Complexes," *Carbohydrate Polymers*, 2002, pp. 19-26, vol. 50, Elsevier Science Ltd.

Lii, C., et al., "Xanthan Gum-Gelatin Complexes," *European Polymer Journal*, 2002, pp. 1377-1381, vol. 38, Elsevier Science Ltd.

Liu, H., et al., "Osteogenic Evaluation of Glutaraldehyde Crosslinked Gelatin Composite with Fetal Rat Calvarial Culture Model," *Artificial Organs*, 2001, pp. 644-654, vol. 25(8), Blackwell Science, Inc.

Liu, L., et al., "An Osteoconductive Collagen/Hyaluronate Matrix for Bone Regeneration," *Biomaterials*, 1999, pp. 1097-1108, vol. 20, Elsevier Science Ltd.

Lou, X. and Chirila, T.V., "Swelling Behavior and Mechanical Properties of Chemically Cross-Linked Gelatin Gels for Biomedical Use," *J. Biomater. Appl.*, 1999, pp. 184-191, vol. 14(2).

Mo, X., et al., "Soft Tissue Adhesive Composed of Modified Gelatin and Polysaccharides," *J. Biomater. Sci. Polymer Edn.*, 2000, pp. 341-351, vol. 11(4), VSP 2000.

Murray, F. and Hutton, P., "Gelling of Urea-Linked Gelatin with Fresh Frozen Plasma," *Anaesthesia*, 1989, pp. 392-393, vol. 44(5).

Naftalin, R.J. and Symonds, M.C., "The Mechanisms of Sugar-Dependent Stabilisation of Gelatin Gels," *Biochim. Biophys. Acta*, 1974, pp. 173-178, vol. 352.

Navarro, F., et al., "Sprayed Keratinocyte Suspensions Accelerate Epidermal Coverage in a Porcine Microwound Model," *J. Burn Care Rehabil.*, 2000, pp. 513-518, vol. 21.

Otani, Y. et al., Effect of Additives on Gelation and Tissue Adhesion of Gelatin-poly(L-glutamic acid) Mixture, *Biomaterials*, 1998, pp. 2167-2173, vol. 19.

Ratner, B., "Reducing Capsular Thickness and Enhancing Angiogenesis Around Implant Drug Release Systems," *J. Control. Release*, 2002, pp. 211-218, vol. 78, Elsevier Science B.V.

Ravin, A., et al., "Long-and Short-Term Effects of Biological Hydrogels on Capsule Microvascular Density Around Implants in Rats," *Journal of Biomedical Material Resources (Applied Biomaterials)*, 2001, pp. 313-318, vol. 58, John Wiley & Sons, Inc.

Sakiyama, S.E., et al., "Incorporation of Heparin-Binding Peptides into Fibrin Gels Enhances Neurite Extension: An Example of Designer Matrices in Tissue Engineering," *FASEB J.*, 1999, pp. 2214-2224, vol. 13(15).

Scholten, E., et al., "Interfacial Tension of a Decomposed Biopolymer Mixture," *Langmuir*, 2002, pp. 2234-2238, vol. 18(6), American Chemical Society.

Sershen, S. and West, J., "Implantable, Polymeric Systems for Modulated Drug Delivery," *Advanced Drug Delivery Reviews*, 2002, pp. 1225-1235, vol. 54, Elsevier Science B.V.

Sutherland, I.W., "Novel and Established Applications of Microbial Polysaccharides," *TIBTECH*, 1998, pp. 41-46, vol. 16.

Tabata, Y. and Ikada, Y., "Vascularization Effect of Basic Fibroblast Growth Factor Released from Gelatin Hydrogels with Different Biodegradabilities," *Biomaterials*, 1999, pp. 2169-2175, vol. 20, Elsevier Science Ltd.

Tromp, R., et al., "Confocal Scanning Light Microscopy (CSLM) on Mixtures of Gelatin and Polysaccharides," *Food Research International*, 2001, pp. 931-938, vol. 34, Elsevier Science Ltd.

Tsai, C., et al., "Effects of Heparin Immobilization on the Surface Characteristics of a Biological Tissue Fixed with a Naturally Occurring Crosslinking Agent (Genipin): An in vitro Study," *Biomaterials*, 2001, pp. 523-533, vol. 22, Elsevier Science Ltd.

Ulubayram, K., et al., "EGF Containing Gelatin-Based Wound Dressings," *Biomaterials*, 2001, pp. 1345-1356, vol. 22.

Van Wachem, P., et al., "(Electron) Microscopic Observations on Tissue Integration of Collagen-Immobilized Polyurethane," *Biomaterials*, 2002, pp. 1401-1409, vol. 23, Elsevier Science Ltd.

Vaz, C., et al., "Use of Coupling Agents to Enhance the Interfacial Interactions in Starch-EVOH/Hydroxylapatite Composites," *Biomaterials*, 2002, pp. 629-635, vol. 23, Elsevier Science Ltd.

Welz, "Examinatin of Self-Crosslinked Gelatin as a Hydorogel for Controlled Release," *Biochemistry*, 1990, pp. 8509-8517, vol. 29.

Wissink, M., et al., "Binding and Release of Basic Fibroblast Growth Factor from Heparinized Collagen Matrices," *Biomaterials*, 2001, pp. 2291-2299, vol. 22, Elsevier Science Ltd.

Wissink, M., et al., "Immobilization of Heparin to EDC/NHS-Crosslinked Collagen. Characterization and in vitro Evaluation," *Biomaterials*, 2001, pp. 151-163, vol. 22, Elsevier Science Ltd.

Zaleskas, J.M., "Growth Factor Regulation of Smooth Muscle Actin Expression and Contraction of Human Articular Chondrocytes and Meniscal Cells in a Collagen-GAG Matrix," *Exp. Cell Res.*, 2001, pp. 21-31, vol. 270.

Zhao, H. and Heindel, N., "Determination of Degree of Substitution of Formyl Groups in Polyaldehyde by the Hydroxylamine Hydrochloride Method," *Pharmaceutical Research*, 1991, pp. 400-402, vol. 8(3), Plenum Publishing Corporation.

Zimmermann, J., et al., "Novel Hydrogels as Supports for in vitro Cell Growth: poly(ethylene glycol)- and Gelatine-Based (meth)acrylamidopeptide Macromonomers," *Biomaterials*, 2002, pp. 2127-2134, vol. 23, Elsevier Science Ltd.

Anonymous: "Halscion Announces European CE Mark Approval of Celotres for Wound Healing and Scar Symptoms," 2012, 1 page. http://halscion.net/halscion-announces-european-ce-mark-approval-of-celotres%e2%84%a2-for-wound-healing-and-scar-symptoms/.

Anonymous: "Halscion Announces Encouraging Data From Klear Feasability Study for Keloid Scars," 2012, 1 page. http://halscion.net/press-release-february-15/2012/.

www.ClinicalTrials.gov, "MF-4181 for the Reduction of Scars Secondary to Abdominoplsty or Laparoscopy/Laparotomy Gynecologic Procedures," Protocol Registration System, Sep. 20, 2011.

www.ClinicalTrials.gov, "Evaluation of the Initial Safety and Efficacy of Keloid Lesions Treated with MF-4181," Protocol Registration System, downloaded Sep. 25, 2011.

Ghosh et al. "Polysaccharide-Protein Interactions and Their Relevance in Food Colloids," *The Complex World of Polysaccharides*, book edited by Desiree Nedra Karunaratne, ISBN 978-953-51-0819-1, Published Oct. 31, 2012, Chapter 14, pp. 395-408.

\* cited by examiner

METHODS AND COMPOSITIONS FOR WOUND TREATMENT

CROSS-REFERENCE TO RELATED APPLICATIONS

The present application claims priority to U.S. Provisional Application No. 61/554,870, filed Nov. 2, 2011, the disclosure of which is incorporated herein by reference in its entirety.

FIELD OF THE INVENTION

The present invention relates to methods and compositions for promoting improved healing of wounds. In particular, the compositions can be effective to modulate the wound healing process so as to promote healing in a manner that can limit hypertrophic healing, scar formation, and keloid formation.

BACKGROUND OF THE INVENTION

There are many situations in medicine where a wound does not heal properly, such as from compromised wound healing that delays or prevents resolution of a wound. There are further wound healing events, however, that can limit resulting function or cosmesis. Exemplary undesired results include hyperplastic responses that produce extensive scarring, keloids, or wound contracture that compromises function and mobility.

Hypertrophic scars occur when the body overproduces collagen, which causes the scar to be raised above the surrounding skin. Hypertrophic scars often take the form of a red raised lump on the skin and usually occur within four to eight weeks following wound infection or wound closure with excess tension and/or other traumatic skin injuries. Keloid formation in particular is a very challenging wound healing problem. Keloids are defined as benign fibrous (fibroblastic or myofibroblastic) proliferations resulting in soft tissue tumors. The benign hyper-proliferative growth of dense fibrous tissue in keloids develops from an abnormal healing response to a cutaneous injury and is dissimilar to normal wound healing and scarring, including hypertrophic scarring. These differences manifest in cellular processes, collagen production and deposition, continued growth beyond the boundaries of the original wound, and a high recurrence rate after excision. Unlike normal scars or hypertrophic scars, keloids contain fibroblasts that overproduce type I procollagen, VEGF, TGFβ1/β2, PDGF-α receptors, and have reduced growth factor requirements, with either lower rates of apoptosis or a down-regulation of apoptotic genes (Robles, et al., *Clinics in Dermatology,* 2007). These aberrant fibroblast processes have demonstrated increased production of collagen and extracellular matrix in vitro and in vivo. X-ray diffraction examination of normal, hypertrophic, and keloid scars demonstrates that rather than the collagen fibrils running parallel to the scar line (normal scar) or slightly aligned to the scar line (hypertrophic scars), the collagen fibrils of keloid scars present no specific orientation of the collagen at all (Koonin eta al., S. A. Medical Journal 1964). Additionally, this collagen has been termed "keloid collagen" since the deposition pattern, mixture of collagen types (greater abundance of type III later replaced by type I), and overabundance are unlike other tissue or scar types (Cheng et al. African Journal of Biotechnology 2011). Finally, unlike normal scars or hypertrophic scars, the propensities for recurrence in keloid scars have been reported at 45-100%, and keloids are resistant to known treatments used for scars or hypertrophic scars (Robles, et al., Clinics in Dermatology 2007).

Compositions to promote wound healing have been described with the use of collagen, the main structural protein of the body. In particular, compositions of collagen combined with a glycosaminoglycan, the structural polysaccharides of the body, have also been described to promote wound healing or act as tissue templates for wound repair. For example, U.S. Pat. No. 4,837,024 describes promoting wound healing by contacting a surface of a wound with a suspension of particles of collagen and a glycosaminoglycan. U.S. Pat. No. 4,280,954 describes a composite material containing collagen and a mucopolysaccharide (glycosaminoglycan) that is useful as a degradable surgical prosthesis such as a synthetic skin Compositions using denatured collagen have also been described in wound healing compositions with polysaccharides. U.S. Pat. No. 6,261,587 and U.S. Pat. No. 6,713,079 describe compositions of gelatin and dextran or heparin to be used to stimulate vascularization and promote wound healing. There still remains a need for methods and compositions useful in wound treatment, particularly in addressing keloids and hypertrophic dermal healing.

SUMMARY OF THE INVENTION

The present invention provides methods and compositions that can be useful in wound treatment to promote healing, and to particularly promote healing in a manner whereby hypertrophic wound healing and/or scar formation is reduced or limited. Thus, the inventive methods and compositions can be particularly useful to reduce or limit scarring including but not limited to post-surgical scars, hypertrophic scars, scars resulting from trauma or burns, and keloids.

In one aspect, the invention thus provides compositions that are useful in treating wounds, such as to reduce or prevent scarring. In one embodiment, the inventive composition can be an aqueous composition comprising gelatin and a polymeric carbohydrate. The composition particularly can exhibit one or more specific conditions. For example, the gelatin can have an average molecular mass that is in a defined range, such as a range of about 75,000 Da or greater, preferably in the range of about 75,000 Da to about 250,000 Da. The polymeric carbohydrate also can have an average molecular mass that is in a defined range, such as a range of about 10,000 Da to about 1,000,000 Da. The gelatin can comprise a specific percentage range or a minimum percentage of the total weight of the combination of the gelatin and the polymeric carbohydrate present in the composition. For example, the gelatin can comprise about 60% by weight or greater of the total weight of the combination of the gelatin and the polymeric carbohydrate present in the composition. Further, the combination of the gelatin and the polymeric carbohydrate can be present in the composition at a specific concentration range. For example, the combination of the gelatin and the polymeric carbohydrate can be present at a total concentration of about 50 mg/mL to about 400 mg/mL. The composition also can have a pH that is in a defined range. For example, the composition can have a pH of about 6 to about 8. The composition particularly can be characterized in relation to its phase controlled nature. Specifically, hydrated forms of the composition can be a flowable, injectable liquid at a temperature of 35° C. or greater and can be a solid or semi-solid gel matrix at lower temperatures.

In a specific embodiment, the invention can be directed to an aqueous composition comprising gelatin and a polymeric carbohydrate, wherein the average molecular weight of the gelatin, the average molecular weight of the polymeric carbohydrate, the weight ratio of the gelatin to the polymeric carbohydrate, and the total concentration of the gelatin and the polymeric carbohydrate are all such that the composition is a flowable liquid at a temperature of 35° C. or greater but is a solid or semi-solid gel matrix at lower temperatures. For example, in some embodiments, the composition can be a solid at a temperature of about 34° C. or less. This property enables the composition to be heated to a temperature where the composition can be injected into the area proximal to a wound (e.g., into the dermal or subdermal tissue partially or completely surrounding the wound) without thermal damage to the tissues and with subsequent transition of the composition to a solid or semi-solid gel matrix to provide a localized environment to aid wound healing. The composition can particularly be a sterile aqueous composition. The polymeric carbohydrate can particularly be a glycosaminoglycan or a synthetic carbohydrate. Even more particularly, the carbohydrate can be dextran or a derivative thereof.

The composition can be provided in a dry form, particularly in a pre-mixed state. The dried composition can take on a variety of physical forms and can be essentially a unitary structure (e.g., a dried sponge-like structure) or can be a plurality of particles ranging in size from several centimeters in diameter to micrometer sized particles or less. Thus, in some embodiments, the dried composition can be considered a powder.

Such dry or lyophilized form can be reconstituted prior to use. More specifically, the composition can be dried, and the dried composition can form a gel after reconstitution with a solvent (e.g., sterile water or buffer solution). Thus, the invention particularly can comprise an aqueous, injectable composition prepared by reconstituting a dried composition comprising: gelatin having a molecular mass as described herein, and a polymeric carbohydrate. Preferably, the gelatin can comprise about 60% by weight or greater of the total weight of the combination of the gelatin and the polymeric carbohydrate present in the composition. Further, the combination of the gelatin and the polymeric carbohydrate can be present in the reconstituted, injectable composition at a total concentration of about 50 mg/mL to about 400 mg/mL. Moreover, the invention can be directed to a composition comprising, in a dried form: gelatin having an average molecular weight of about 75,000 Da to about 250,000 Da; and a polymeric carbohydrate. Preferably, in such composition, the gelatin can comprise about 60% by weight or greater of the total weight of the combination of the gelatin and the polymeric carbohydrate present in the composition. Further, the composition can be reconstitutable in a solvent (e.g., sterile water or a buffer solution) to form a flowable, injectable liquid. In even further embodiments, the invention can be directed to a composition comprising gelatin and a polymeric carbohydrate in a ratio and amounts such that, upon reconstitution with a solvent, the hydrated composition is a flowable, injectable liquid at a temperature of 35° C. or greater but is a solid or semi-solid gel matrix at lower temperatures.

In specific embodiments, a composition according to the present disclosure can comprise gelatin having an average molecular mass of about 75,000 Da to about 250,000 Da and a polymeric carbohydrate having an average molecular mass of about 10,000 Da to about 1,000,000 Da. Preferably, a hydrated form of the composition is a flowable, injectable liquid at a temperature of 35° C. or greater and is a solid or semi-solid gel matrix at lower temperatures. Particularly, the hydrated form of the composition can have a differential scanning calorimetry curve exhibiting a peak at about 35° C. to about 37° C. Moreover, the gelatin can comprise about 60% by weight or greater of the total weight of the combination of the gelatin and the polymeric carbohydrate present in the composition. Further, the total concentration of the gelatin and the polymeric carbohydrate in the hydrated form of the composition can be about 50 mg/mL to about 400 mg/mL. In certain embodiments, the flowable, injectable liquid can have a flow rate of about 10 µL/s or greater when forced from a syringe through a 16 mm (⅝ inch) long 25 gauge needle under a syringe plunger pressure of 5 N at a temperature of 35° C. to 39° C. The hydrated, flowable composition also can be characterized in relation to further physical properties. For example, the flowable liquid can have a solids concentration of about 0.5 g/mL or less and can have a viscosity of about 1.5 Pa·s or less at a temperature of 35° C. to 39° C. A solid or semi-solid gel matrix at ambient conditions can have a compressive modulus of about 15 kPa or greater (when evaluating a disc of 1 cm diameter and 1 cm thickness). Preferably, the composition can have a fibronectin binding activity of about 3 nmol/mg or greater. The composition also can be characterized in relation to residence time in the dermal or subdermal tissue of a mammal (e.g., a human), and such time can be, in some embodiments, about 3 days or greater. In certain embodiments, the solid or semi-solid gel matrix of the invention exhibits one or both of: i) a compressive modulus of greater than about 34 kPa at ambient conditions when in the form of a disc of 1 cm diameter and 1 cm thickness; and ii) a time to complete dissolution of at least about 45 minutes in phosphate buffered saline at 34° C. when in the form of a disk of 8 mm diameter and 1.5 mm in height.

The composition can include a variety of further components. For example, the composition can include one or more of a surfactant, a hygroscopic excipient, a buffer, and a bulking agent. Such additives can be included in the originally prepared composition or can be added to a lyophilized composition during reconstitution. The composition further can include one or more amino acids and one or more salts.

In another aspect, the present disclosure further provides methods for the manufacture of a composition for wound treatment and scar prevention and minimization, particularly a composition comprising gelatin and a polymeric carbohydrate. In some embodiments, such method of manufacture can comprise combining the gelatin, the polymeric carbohydrate, and a solvent with mixing so as to progressively solubilize the gelatin and the polymeric carbohydrate and form a hydrated matrix composition. The gelatin can have an average molecular mass of about 75,000 Da to about 250,000 Da, and the polymeric carbohydrate can have an average molecular mass of about 10,000 Da to about 1,000,000 Da. Further, the gelatin can comprise about 60% by weight to about 95% by weight of the total weight of the combination of the gelatin and the polymeric carbohydrate present in the composition, and the total concentration of the gelatin and the polymeric carbohydrate in the hydrated form of the composition can be about 50 mg/mL to about 400 mg/mL.

The method can further comprise removing a fraction of lower solubility in the solvent from either i) one or both of the gelatin and the polymeric carbohydrate before the combining step; or ii) the hydrated matrix composition formed in the combining step, in order to increase the average molecular mass of one or both of the gelatin and the polymeric carbohydrate. Accordingly, this step would result in concentrating the composition toward fractions of lower solubility of one or both of the gelatin and the polymeric carbohydrate. In other words, the most soluble fractions can be removed to concentrate the less soluble fractions of the composition during mixing. Such removal can be performed, for example, by decanting or removal of a liquid phase during progressive solubilization. More specifically, removal can be via filtration. In other embodiments, the removal can be performed by partially insolubilizing the mixture and removing the liquid fraction. Such insolubilization can be performed by the addition of an organic solvent or can be performed by exposing the polymeric components to a high ionic strength solution. In further embodiments, the resultant composition after concentration can have a higher average molecular mass of gelatin than the composition prior to concentration. Likewise, the resultant composition after concentration can have a higher average molecular mass of polymeric carbohydrate than the composition prior to concentration. The composition can be dried, such as by lyophilization, such that the composition is in a dried form, particularly a reconstitutable mass, powder, or the like. For example, the composition can be dried to a liquid content of about 5% or less, about 4% or less, about 3% or less, about 2% or less, about 1% or less, or about 0.5% or less.

In further aspects, the invention also can be directed to methods of treatment (or use of the various compositions). In some embodiments, the invention can be directed to methods for prevention, minimization, or treatment of a scar. Such methods can comprise injecting an aqueous composition as described herein and that is heated to a flowable temperature into the dermal or subdermal tissue in the proximity of a wound, a surgically revised hypertrophic scar or keloid, existing scar, or keloid. Such injecting particularly can be carried out following a surgical procedure, during surgical revision of a scar, or during treatment of an existing scar, a chronic wound, or a traumatic wound. In further embodiments, the invention can be directed to methods for improving the appearance of an existing scar or keloid. Such methods can comprise: excising at least a portion of the hypertrophic scar or keloid; and injecting a flowable composition as described herein into the dermal or subdermal tissue in the proximity of the hypertrophic scar/keloid or the excision site. In other embodiments, the invention can be directed to methods for treatment of a surgical wound. Such methods can comprise injecting a flowable composition as described herein into the dermal or subdermal tissue in the proximity of the surgical wound. In even further embodiments, the invention can be directed to methods for preventing or reducing scarring arising from a surgically created wound. Such methods can comprise injecting a flowable composition as described herein into the dermal or subdermal tissue in the proximity to the surgically created wound.

In specific embodiments according to the present disclosure a method for preventing or reducing cutaneous scarring, or an effect thereof, arising from a cutaneous wound can comprise applying a matrix composition to the cutaneous wound. The matrix composition particularly can comprise gelatin having an average molecular mass of about 75,000 Da to about 250,000 Da, and a polymeric carbohydrate having an average molecular mass of about 10,000 Da to about 1,000,000 Da. Further, a hydrated form of the matrix composition can be a flowable, injectable liquid at a temperature of 35° C. or greater and a solid or semi-solid gel matrix at lower temperatures. The method further can comprise closing the wound with a closure selected from the group consisting of sutures, staples, glue, and combinations thereof. The applying step can comprise injecting the flowable, injectable liquid composition into dermal or subdermal tissue in proximity to the cutaneous wound. Further the injecting can comprise injecting the flowable, injectable liquid composition through a relatively small needle (e.g., 18 gauge to 27 gauge in size or 23 gauge to 25 gauge in size). In certain embodiments, the applying step can comprise delivering about 0.1 mL to about 10 mL of matrix composition per 2.5 cm of wound margin.

In further embodiments, the cutaneous wound can be a surgical wound. For example, the surgical wound can be a wound remaining after excision of at least a portion of a pre-existing scar. Thus, the method can comprise the step of excising at least a portion of the pre-existing scar. The excised scar particularly can be a keloid scar, a hypertrophic scar, or a burn-related scar. Thus, the cutaneous wound can be a burn. Moreover, the applying step can comprise topical application of the matrix composition.

The matrix composition in some embodiments can be in a lyophilized form. Thus, prior to applying the composition, the method can comprise reconstituting the lyophilized matrix composition. Specifically, reconstituting can comprise combining the matrix composition with an additive— e.g., selected from the group consisting of polyols, polysorbates, physiological salts, monosaccharides, sugar alcohols, and combinations thereof.

In particular embodiments, the present disclosure provides methods specifically for the revision of a cutaneous keloid or hypertrophic scar. Such methods can comprise excising at least a portion of the keloid or hypertrophic scar tissue so as to form an excision site, and applying a matrix composition as described herein to the dermal or subdermal tissue in or around the excision site. The methods further can comprise closing the excision site with a closure—e.g., selected from the group consisting of sutures, staples, glue, and combinations thereof. In other embodiments, the applying step can comprise injecting the flowable, liquid matrix composition into the dermal or subdermal tissue around the excision site.

In other embodiments, the present disclosure provides methods specifically for reducing the external volume of a cutaneous keloid or hypertrophic scar. Such methods can comprise excising at least a portion of the keloid or hypertrophic scar tissue so as to form an excision site, and applying a matrix composition as described herein to the dermal or subdermal tissue in or around the excision site. Arising from the nature of the disclosed compositions (as discussed in detail herein), the external volume of any scar tissue present 12 months after said excision and application of the matrix composition relative to the external volume of the excised keloid or hypertrophic scar can be quantified and can be, for example, about 15% or less.

DETAILED DESCRIPTION OF THE INVENTION

Figure 1:
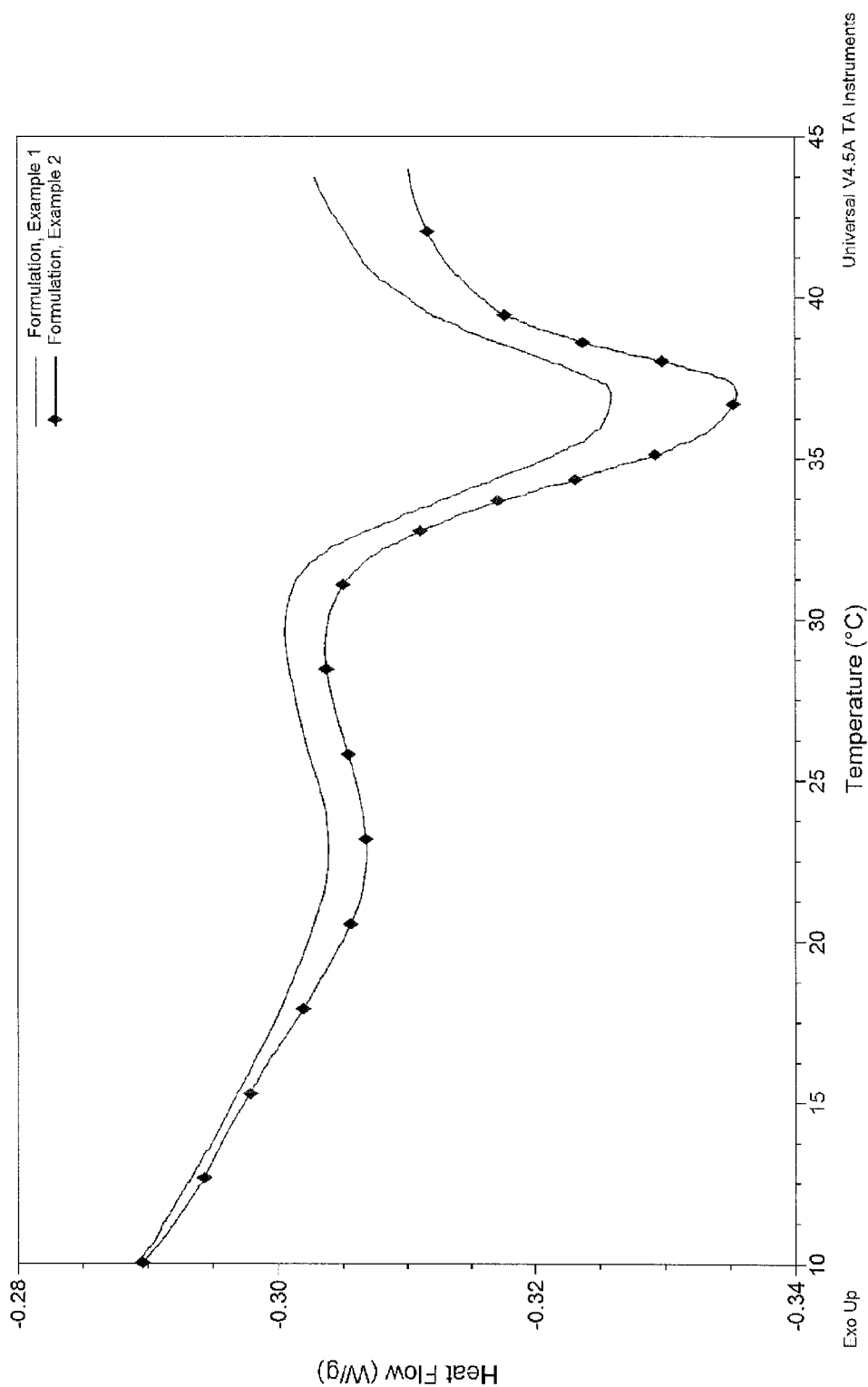
FIG. 1 is a graph showing a differential scanning calorimetry curve for exemplary compositions according to the present disclosure.

The present invention will now be described more fully hereinafter with reference to exemplary embodiments thereof. These exemplary embodiments are described so that this disclosure will be thorough and complete, and will fully convey the scope of the invention to those skilled in the art. Indeed, the invention can be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

The present disclosure relates to compositions that are beneficial for use in the treatment of wounds, particularly wounds to the skin (i.e., the dermis). While the average core body temperature of a human is 37° C. (+/−0.5° C.), skin temperatures can be significantly lower and typically are in the range of about 33° C. (+/−1° C.). The present disclosure describes compositions formed of gelatin and a polymeric carbohydrate that can be provided in a variety of forms and thus can be particularly useful in treating skin wounds. More specifically, the gelatin and the polymeric carbohydrate can be combined such that the interaction of the gelatin and the carbohydrate forms a solid or semi-solid gel matrix composition at temperatures that are about equal to or below average skin temperature. As more fully discussed below, the composition can be a solid or semi-solid material at a temperature that is less than 35° C.

In the dermal or subdermal tissue, the composition is substantially in the form of a solid or semi-solid gel matrix that modulates wound healing by its physical presence and potential interactions of the gelatin and the polymeric carbohydrate during the wound healing and wound maturation process. The composition of the present disclosure biodegrades and/or is physiologically resorbed by the tissues surrounding the implanted matrix composition. Thus, the solid or semi-solid matrix composition has a defined residence time during which the composition improves wound healing and slowly degrades. The composition also can be provided in a dried (e.g., powder) form that is particularly useful for long-term storage of the composition. Such powder compositions can be reconstitutable using a variety of physiologically acceptable solvents and additives.

While the invention is not bound by a particular mechanism, it is believed that the combined gelatin and polymeric carbohydrate provides an environment that is similar to the native wound healing environment (e.g., in the presence of collagen and glycosaminoglycans). Such an environment can reduce or limit hypertrophic wound healing, including hypertrophic scar formation and keloid formation.

The compositions of the present disclosure provide the advantage of being a flowable (and injectable) liquid at temperatures that are only slightly above average dermal temperature and thus can be injected without thermal damage to the interfacing tissues. The compositions provide the further advantage, however, of transitioning into a solid or semi-solid gel matrix at about average dermal temperatures and thus can exhibit sufficient persistence at the vicinity of a dermal wound to have beneficial effect during the wound healing process. Preferably, the composition can be degradable but can persist during the acute wound healing period, e.g., approximately two weeks, but can remain for a longer period of time to benefit collagen maturation and wound remodeling. The composition can be useful for the treatment of keloid scars, hypertrophic scars, burn-related scars, or for the prophylactic treatment of surgical wounds, particularly in patients prone to scar formation. Patients falling into such categories can be identified based upon past history of scar formation—e.g., hypertrophic scarring or keloid formation. Additionally, patients can be identified based upon characterization into a group that is recognized in the art as being at increased risk for keloid formation (i.e., darkly pigmented skin). For example, there is a fifteen times higher frequency of keloid occurrence in highly pigmented people as compared to less pigmented people. More specifically, persons of African descent are recognized as being at increased risk of keloid occurrences.

The compositions of the present disclosure can be particularly characterized in relation to specific properties thereof. For example, during production of gelatin, a variety of chemical processes are used to degrade the collagen that can also degrade the fibronectin and polymeric carbohydrate binding properties of the resultant gelatin. To have the desired properties, the composition is preferred to comprise a gelatin with intact fibronectin binding activity. To this end, it can be preferential to use a gelatin of a defined molecular mass. Specifically, the gelatin can have an average molecular mass of about 75,000 or greater, about 80,000 Da or greater, about 100,000 Da or greater, or about 110,000 Da or greater. In specific embodiments, the gelatin can have an average molecular mass of about 75,000 Da to about 250,000 Da, about 90,000 Da to about 225,000 Da, about 100,000 Da to about 200,000 Da, or about 120,000 Da to about 180,000 Da. In specific embodiments, a gelatin having a molecular mass of 140,000 Da to about 160,000 Da can be particularly useful.

Molecular mass can be expressed as a weight average molecular mass ($M_w$) or a number average molecular mass ($M_n$). Both expressions are based upon the characterization of macromolecular solute containing solution as having an average number of molecules ($n_i$) and a molar mass for each molecule ($M_i$). Accordingly, number average molecular mass is defined by formula 1 below.

$$M_n = \frac{\sum n_i M_i}{\sum n_i} \tag{1}$$

Weight average molecular mass (also known as molecular mass average) is directly measurable using light scattering methods and is defined by formula 2 below.

$$M_w = \frac{\sum n_i M_i^2}{\sum n_i M_i} \tag{2}$$

Molecular mass can also be expressed as a Z-average molar mass ($M_Z$), wherein the calculation places greater emphasis on molecules with large molar masses. Z-average molar mass is defined by formula 3 below.

$$M_z = \frac{\sum n_i M_i^3}{\sum n_i M_i^2} \tag{3}$$

Unless otherwise noted, molecular mass is expressed herein as weight average molecular mass.

The gelatin used according to the invention can be derived from a variety of useful sources, such as that obtained by at least partially hydrolyzing collagen that is derived from animal skin, connective tissue, or bones. Alternatively, the gelatin can be from in vitro synthesis, such as from cell culture, can be human-derived, or can be synthetic. Type A gelatin (i.e., derived from an acid-treated precursor) or Type B gelatin (i.e., derived from an alkali-treated precursor) can be used. Moreover, the gelatin can be derived using chemical hydrolysis and/or thermal hydrolysis to denature the collagen.

The polymeric carbohydrate of the composition can be a natural carbohydrate, such as a glycosaminoglycan or can be a synthetic carbohydrate. To have the desired properties to form a solid or semi-solid gel matrix at the desired temperatures with gelatin, a carbohydrate (e.g., dextran) having a molecular mass of approximately 10,000 to 1,000,000 Da can be preferred. Carbohydrates with a molecular mass at the higher end of the range can provide greater matrix physical properties and stability.

The polymeric carbohydrate can encompass a variety of polysaccharides, such as glycosaminoglycans or mucopolysaccharides, and synthetic carbohydrates. Specific, non-limiting examples of polymeric carbohydrates that can be used include agarose, alginate, amylopectin, amylose, carrageenan, cellulose, chitin, chitosan, chondroitin sulfate, dermatan sulfate, dextran, dextran sulfate, glycogen, heparan, heparan sulfate, heparin, hyaluronic acid, keratan sulfate, and starch.

The stoichiometry of the gelatin and the polymeric carbohydrate preferably can be formulated in a desirable range due the complementary ionic charges of the two polymeric components at physiological pH. Since the desired physical and potential biological properties are derived from the polymeric components (gelatin plus polymeric carbohydrate), the preferred stoichiometry range is a minimum of 60% of the polymeric weight comprising gelatin to provide suitable properties as described in the examples. Thus, the gelatin component can comprise about 60% or greater by weight of the combination of the gelatin and the polymeric carbohydrate. In further embodiments, the gelatin component can comprise about 62% or greater, about 65% or greater, about 67% or greater, or about 70% or greater by weight of the combination of the gelatin and the polymeric carbohydrate. In further embodiments, the gelatin can comprise about 60% by weight to about 95% by weight, about 65% by weight to about 90% by weight, or about 70% by weight to about 85% by weight of the combination of the gelatin and the polymeric carbohydrate in the overall composition.

As already noted above, the overall combination of materials forming the present composition, including the aqueous component, can provide for the formation of a material that has a relatively narrow phase change temperature range. Specifically, the interaction of the polymeric materials and the additional components of the composition can form a phase-controllable hydrogel matrix that is solid or semi-solid at temperatures approximately equal to the average skin temperature or below and that can be transitioned to a flowable liquid composition by heating to a temperature that is slightly greater than average skin temperature. In other words, the presently disclosed compositions can provide surprisingly narrow phase control. Specifically, the present compositions can be tailored to have a very narrow and specific transition temperature range such that a difference of, for example, only about 0.5° C. to about 3° C., about 0.8° C. to about 2.5° C., or about 1° C. to about 2° C., can be effective to cause the phase transition from solid or semi-solid to flowable liquid (or vice versa). In certain embodiments, the presently disclosed hydrated composition can be a flowable liquid at a temperature of 35° C. or greater, as determined by differential scanning calorimetry (DSC). More particularly, the presently disclosed composition can be a flowable liquid at a temperature of 35° C. or greater, about 36° C. (+/−0.5° C.) or greater, or about 37° C. (+/−0.5° C.) or greater. In other embodiments, the presently disclosed composition can be in a solid or semi-solid gel matrix at a temperature that is less than 35° C.

The total polymer concentration of gelatin and polymeric carbohydrate can range from approximately 50 mg/mL to approximately 400 mg/mL, approximately 75 mg/mL to approximately 350 mg/mL, or approximately 100 mg/mL to approximately 300 mg/mL. The composition can be titrated to near physiological pH to allow the ionic interactions of the two polymeric components to form a gel. Buffers can be utilized to promote the appropriate pH, in the range of about 6 to about 8. Other components such as physiological salts and amino acids can be incorporated into the composition to provide a supportive environment for cells involved in wound healing. Exemplary amino acids that can be used include Glutamic acid, Arginine, Lysine, Cysteine, and Alanyl-Glutamine A specific isomer, such as the L-isomer, of the amino acids can be used. Exemplary useful salts include edatate disodium and metal salts, such as zinc salts (e.g., zinc sulfate), calcium salts, magnesium salts, sodium salts, and potassium salts.

The compositions of this disclosure are particularly useful in that when they are heated to temperatures that are slightly above average human dermal temperature (i.e., 35° C. or greater), the compositions shift from being a solid or semi-solid material into a flowable liquid. Preferably, the flowable liquid composition exhibits suitable physical characteristics to allow for injection of the composition into the dermal and subdermal tissues, such as those surrounding a dermal wound. In specific embodiments, the physical characteristics are such that the flowable liquid composition is adapted for injection through a relatively small gauge needle. For example, the flowable liquid composition can be adapted to injection through a needle or the like having a nominal inner diameter of about 0.2 mm or greater, about 0.25 mm or greater, or about 0.3 mm or greater. The flowable liquid composition further can be adapted to injection through a needle or the like having a nominal inner diameter of about 0.2 mm to about 0.4 mm or about 0.25 mm to about 0.35 mm Examples of useful needle gauges include 18 gauge through 27 gauge needles, 23 gauge through 27 gauge needles, or 23 gauge through 25 gauge needles. Since relatively small gauge needles are required to inject a composition into a relatively small target, such as that presented by dermal tissues, it is necessary for injectable compositions to exhibit sufficiently low viscosities. Also, injectable compositions must limit colloidal or insoluble particles to those in a size range that is less than the nominal inner diameter of the injection needle. Thus, it can be beneficial for colloidal or insoluble particles to have an average size that is about one-fifth or less, about one-sixth or less, or about one-eighth or less than the nominal inner diameter of the injection needle. More specifically, the colloidal or insoluble particles can have an average size of about one-fifth to about one-tenth the nominal inner diameter of the injection needle. Such sizing can allow for injection of the composition without needle clogging.

Total solids content similarly can adversely affect flowability and injectability of the present composition. Preferably, when in a flowable, liquid form, it can be desirable for the composition to have a total solids content below a certain threshold, particularly to provide a viscosity suitable for injection through a small gauge needle. For example, it can be beneficial for total solids content to be about 0.5 g/mL or less, about 0.4 g/mL or less, about 0.3 g/mL or less, about 0.2 g/mL or less, or about 0.1 g/mL or less. In further embodiments, the total solids content of the flowable, injectable liquid composition can be about 0.01 g/mL to about 0.5 g/mL, about 0.025 g/mL to about 0.45 g/mL, about 0.05 g/mL to about 0.4 g/mL, or about 0.1 g/mL to about 0.3 g/mL.

Still further to the above, the viscosity of the flowable, liquid composition according to the present disclosure can be relevant to injectability of the material—e.g., through a small gauge needle. More specifically, a significantly high viscosity can limit the ability to inject the composition through with a manual syringe. Preferably, when in a flowable, liquid form, it can be desirable for the composition to have a viscosity of about 2 Pa·s or less, about 1.5 Pa·s or less, about 1.25 Pa·s or less, about 1.1 Pa·s or less, about 1 Pa·s or less, about 0.75 Pa·s or less, about 0.5 Pa·s or less, or about 0.25 Pa·s or less. In further embodiments, a flowable, liquid composition can have a viscosity of about 0.01 Pa·s to about 2 Pa·s, about 0.025 Pa·s to about 1.75 Pa·s, about 0.05 Pa·s to about 1.5 Pa·s, about 0.1 Pa·s to about 1.25 Pa·s, or about 0.2 Pa·s to about 1.1 Pa·s. One method for evaluating viscosity is described below in Example 4, and viscosity values can be referenced to a test temperature range of about 39° C.

The flowability of the hydrated, liquid composition can be characterized in relation to the pressure and flow rate of the composition through a needle. For example, flow rate can be evaluated through use of known fluid dispensing systems, such as those available from Nordson/EFD. In a specific test, 1 mL of a test fluid can be placed in a 1 mL syringe and a syringe plunger force of 5 Newtons (N) can be applied to force the fluid out of the syringe through a 16 mm (⅝ inch) long 25 gauge needle (0.26 mm nominal inner diameter). Such testing is in accord with ISO 7886-1, but other testing conditions also can be used. When the above testing conditions are used, a liquid, hydrated composition according to the present disclosure can have an average flow rate of about 5 µL/s or greater, about 10 µL/s or greater, about 15 µL/s or greater, about 25 µL/s or greater, about 75 µL/s or greater, about 100 µL/s or greater, or about 200 µL/s or greater. Average flow rate particularly can be about 10 µL/s to about 400 µL/s, about 12 µL/s to about 350 µL/s, or about 15 µL/s to about 300 µL/s. The above values similarly can apply to flowability through any gauge needle otherwise described herein. Further, such values for flowability can be referenced to a test temperature range of about 39° C.

When in the solid or semi-solid state, the compositions of the present disclosure can be characterized by the compressive strength of the material. Mechanical testing to evaluate mechanical strength is particularly described below in Example 6, and such testing can be carried out using materials and methods available in the industry. In certain embodiments, a solid or semi-solid composition according to the present disclosure can exhibit a compressive modulus of about 15 kPa or greater, about 20 kPa or greater, or about 25 kPa or greater at ambient conditions. In other embodiments, compressive modulus can be about 15 kPa to about 50 kPa, about 20 kPa to about 45 kPa, or about 20 kPa to about 40 kPa at ambient conditions. In certain further embodiments, the compressive modulus can be characterized as at least about 34 kPa, at least about 35 kPa, or at least about 36 kPa at ambient conditions. In some embodiments, the manufacturing process according to the invention can produce compositions of the invention with relatively high levels of compressive modulus, which may enhance performance of such materials in certain wound treatments. One method for evaluating compressive modulus is discussed in Example 6.

When in the solid or semi-solid state, the compositions of the present disclosure can also be characterized by the dissolution properties of the material. Testing to evaluate dissolution of the materials of the invention is particularly described below in Example 6, and such testing can be carried out using materials and methods available in the industry. In certain embodiments, the composition of the invention formed in disks (sized 8 mm in diameter and 1.5 mm in height) can exhibit complete dissolution, according to visual inspection in phosphate buffered saline at 34° C., in greater than about 45 minutes, greater than about 46 minutes, greater than about 47 minutes, or greater than about 48 minutes. Greater resistance to dissolution generally correlates to enhanced residence time when implanted at a wound site, which may enhance the wound healing function of the compositions of the invention.

The compositions of the present disclosure can be particularly beneficial in relation to the preserved activity of specific components thereof. As discussed above, the process of denaturing collagen (e.g., the chemical processing) can degrade the fibronectin and polymeric carbohydrate binding properties of the resultant gelatin. This can in part relate to the degradation of the alpha chains of the collagen. The compositions of the present disclosure, however, in part because of the preservation of the higher molecular mass collagen alpha chains, can exhibit high fibronectin binding activity (FBA), particularly in comparison to other compositions comprising denatured collagen. In certain embodiments, compositions according to the present disclosure can exhibit a FBA of about 3 nmol/mg or greater, about 4 nmol/mg or greater, or about 5 nmol/mg or greater. Such activity can be measured as the concentration of fibronectin binding sites on the gelatin normalized to the concentration of the gelatin in the composition. One method for measuring fibronectin binding activity is described in Example 5.

As further discussed below, the compositions of the present disclosure particularly can be used in the treatment of the dermal or subdermal tissue of mammals, particularly humans. Generally, the flowable compositions can be injected into an area of the dermal or subdermal tissue, such as in the area of a new, healing, or healed wound. As such, the compositions can be characterized in relation to the residence time of the intact composition within the dermal or subdermal tissue. Such residence time of the composition can also be referred to as the biodegradability time of the composition—i.e., the amount of time from placement until the materials of the composition are degraded or bioabsorbed by the surrounding tissue and physiological processes. In certain embodiments, the residence time of a composition according to the present disclosure in the dermal or subdermal tissue of a mammal, such as a human, can be about 3 days or greater, about 4 days or greater, about 5 days or greater, about 6 days or greater, or about 7 days or greater. In other embodiments, the residence time can be about 3 days to about 60 days, about 4 days to about 45 days, about 5 days to about 40 or about 6 days to about to about 35 days.

In preparation of the composition of the present disclosure, the polymeric components can be mixed together with sufficient water (or other solvent) to allow the polymers to interact. The polymers can be added to a mixing vessel dry and then hydrated together, or separate solutions of the individual polymers can be prepared and then be mixed together. Buffers or titrating agents can be added to adjust the pH and ionic strength. The combination of components can then be mixed with heating (e.g., to a temperature greater than the liquid transition temperatures discussed herein) to form a uniform composition. During the processing, specific methods can be utilized to tailor the composition to further increase desirable properties.

To promote stability of the resultant gel matrix, it can be desirable to concentrate the portions of the polymers that contribute to the stability of the final composition in-situ. Methods can be used in production of the composition to remove the most soluble portions of each polymer or of the mixed composition to concentrate the portions of each polymer with the desired properties. One method to concentrate the desired polymer can be to slowly solubilize the polymers together while heating and to decant or remove the most soluble liquid to concentrate the remaining polymer mixture. Another method to concentrate the composition can be to wash each polymer or the mixture of the polymers while in a partially soluble condition, such as due to exposure with water/alcohol mixture or with high ionic strength conditions such as with NaCl solutions. Such gel washing techniques can result in a composition that retains the less soluble components and thus enhances physical properties of the composition and improves persistence in the treatment site. It is particularly beneficial to concentrate the composition while the polymers are mixed in the desired pH range to allow ionic interactions between the polymers and fractionation to remove the more soluble portions of the polymer composition.

Bulk fractionation methods known in the art can be used to concentrate the polymers as discussed above. For example, size exclusion chromatography (e.g., gel filtration chromatography or gel permeation chromatography) or Baker-Williams fractionation. Further fractionation methods that can be useful in preparation of the present compositions can be found in Francuskiewicz, *Polymer Fractionation*, Springer-Verlag, 1994, the disclosure of which is incorporated herein by reference in its entirety. Such fractionated compositions are expected to have greater stability and improved physical properties when in a solid or semi-solid state.

The composition of the disclosure can also include other active agents to either facilitate its use, or to enhance its beneficial effect on a site in need of treatment. Such active agents can include hemostatic agents (including collagen or thrombin), antimicrobial agents (including antibiotics), bacteriocidal or bacteriostatic agents, growth factors (including epidermal growth factor, fibroblast growth factor, platelet derived growth factor, or insulin-like growth factor), or anti-inflammatory agents (such as corticosteroids or non-steroidal anti-inflammatory agents).

To facilitate shipping and storage at ambient conditions, the composition can be lyophilized to a dry state and reconstituted or rehydrated prior to use. The lyophilized composition can provide improved stability and allow room temperature storage prior to use. Exemplary lyophilization methods that can be used according to the invention are disclosed in the following: U.S. Pat. No. 5,192,743; U.S. Pat. No. 7,666,413; U.S. Pat. No. 7,695,736; and US Patent Publication No. 2008/0145404. The disclosures of all of the preceding documents are incorporated herein by reference in their entireties. Due to the unique use of the composition, the formulation for lyophilization can be tailored to enable rapid reconstitution of the product. For example, reconstitution can be substantially complete within a time of about 30 seconds to about 90 minutes. In specific embodiments, the time to substantially complete reconstitution can be about 90 minutes or less, about 60 minutes or less, or about 45 minutes or less. The time for reconstitution particularly can be in the range of about 15 minutes to about 90 minutes or about 30 minutes to about 60 minutes. Heating can be applied during reconstitution and/or the liquid used for reconstitution can be pre-heated to a specific temperature. For example heating to a temperature of 35° C. or greater can be beneficial. Preferably the reconstitution comprises the addition of an aqueous solution to the lyophilized composition and mixing without the use of mixing methods that would require opening of the container containing the composition and aseptic handling which would complicate use by medical personnel. Means to facilitate reconstitution can include formulation of the composition in a dilute concentration to result in a lower density and more porous dry material. The dried material subsequently can be rehydrated with less fluid than was required to prepare the composition for lyophilization.

The compositions according to the present disclosure can include further components that particularly can be beneficial for reconstitution of the lyophilized material. For example, surfactants can be utilized to minimize hydrophobic interactions within the lyophilized composition that may limit water penetration necessary for reconstitution. Non-limiting examples of suitable surfactants include anionic surfactants (e.g., fatty acids, salts of fatty acids, and alkyl sulfates including sodium lauryl sulfate), cationic surfactants (e.g., ceramide), non-ionic surfactants (e.g., polyol esters, polyoxyethylene esters, and polysorbates, including polysorbate 20 and polysorbate 80), and amphoteric or zwitterionic surfactants. As further examples, hygroscopic excipients also can be used, such as polyethylene glycol, polyols (e.g., glycerin), polysorbates, cyclodextrins, sodium chloride, potassium chloride, magnesium chloride, calcium chloride, and zinc chloride. Such materials can be added to the initially prepared hydrogel (i.e., before lyophilization) or can be added during reconstitution.

As noted above, buffer solutions can be utilized in the preparation of the hydrogel matrix compositions, and appropriate buffers can be added during formation of the initial composition and/or reconstitution of the lyophilized composition. Exemplary buffers that can be used include tris (hydroxymethyl)aminomethane, citrate, glycine, and 4-(2-hydroxyethyl)-1-piperazineethanesulfonic acid. Further, preservatives can be added and can be useful to preserve the composition during dehydration or lyophilization. Likewise, a variety of bulking agents can be utilized in the preparation of the initial hydrogel matrix composition and/or can be added during reconstitution of the lyophilized composition. Although not wishing to be bound by theory, it is believed that the addition of such bulking agents can lead to a lyophilized product that can be more easily penetrated by the water or other solvent used for reconstitution. Exemplary bulking agents that can be used include monosaccharides and disaccharides (for example, dextrose, sucrose, or trehalose), and sugar alcohols, such as mannitol.

In some embodiments, certain surfactants, hygroscopic excipients, buffers, and bulking agents (or combinations thereof) can be useful to improve the lyophilization conditions, facilitate preservation after lyophilization, and/or improve the properties of the reconstituted material. Preferred additives for reconstitution can be those that do not interfere with the ability to the composition to form a flowable and injectable fluid at elevated temperature and a solid or semi-solid hydrogel matrix at skin (i.e., dermal and/or subdermal) temperatures, particularly over a narrow, controlled phase change temperature. For example, polyols (e.g., glycerol), polysorbates (e.g., polysorbate 20 or polysorbate 80), salts (e.g., physiological salts, such as sodium chloride), and sugars (e.g., monosaccharides such as dextrose) can provide specific improvements in various properties of the reconstituted material, as noted above.

The present disclosure also provides various methods of treatment whereby the compositions can be applied to cutaneous wounds, including surgical incisions and excision sites, to improve the healing process of the wound and thus prevent or reduce the occurrence of scarring, including hypertrophic scarring and keloid scarring, and prevent or reduce an effect of scarring. Application of the compositions of the present disclosure can vary depending upon the nature of the treatment site and can include topical application as well as injection, such as into the dermal or subdermal tissue in the proximity of the wound (i.e., along one side of the wound or partially or completely surrounding the wound). When injection is used, the composition particularly can be adapted for injection through a small gauge needle (e.g., such as 23 gauge, 25 gauge, or 27 gauge), as already discussed above. In addition to application of the composition, the methods also can include closing the wound, such as using a closure selected from the group consisting of sutures, staples, glues, and combinations thereof.

In some embodiments, the methods can encompass application to an accidental wound, such as a cut or a burn to the skin, or a chronic wound. In other embodiments, the methods can encompass application to a surgically created wound, such as a surgical incision. Specifically, the surgical wound can be a wound remaining after excision of a pre-existing scar (e.g., a hypertrophic scar, a keloid scar, or a burn-related scar).

In specific embodiments, the disclosed methods can include methods for the revision of a cutaneous keloid or hypertrophic scar (or other types of scars, including burn-related scars). A hypertrophic scar may be characterized as a raised scar arising from overproduction of collagen. A keloid may be characterized as a benign fibrous proliferation resulting in a large hyperplastic mass or soft tissue tumors. Such revision method can comprise excising at least a portion of the scar tissue so as to form an excision site (i.e., a site from which tissue has been surgically removed). The methods further can comprise applying a matrix composition as described herein to the dermal or subdermal tissue in and/or around the excision site. Thus, the composition can be applied directly to the exposed tissue within the excision site and/or the composition can be injected to the surrounding tissue, as described above.

The amount of the composition applied can vary based upon the dimensions of the treatment area. In some embodiments, the hydrated composition can be applied in a volume relative a dimension of the wound. For example, relative volumes can reference the wound margin (i.e., each side of an incision). In some embodiments, total volume of application can be in an amount of about 0.1 mL to about 100 mL, about 0.5 mL to about 75 mL, or about 1 mL to about 50 mL. In other embodiments, the hydrated composition an be applied in a relative volume of about 0.1 mL to about 10 mL per 2.5 cm of the wound margin, about 0.2 mL to about 8 mL per 2.5 cm of the wound margin, about 0.25 mL to about 6 mL per 2.5 cm of the wound margin, or about 0.5 mL to about 4 mL per 2.5 cm of the wound margin. If desired, the methods further can comprise closing the excision site with one or more closures. The closure, for example, can comprise staples, sutures, and glues. In various embodiments, the composition can be injected before and/or after closure.

Scars of significant size can cause pain or discomfort and can be a source of social anxiety or embarrassment. Surgical scar revision according to the present disclosure can be particularly beneficial in that a pre-existing scar can not only be removed, but the recurrence of the scar can be prevented or reduced. It is recognized in the field that patients that have previously been prone to hypertrophic scarring or keloid formation are likely to experience recurrence of scars of a similar size and nature even after revision surgery. Studies have shown that recurrence is seen in at least 50% of revision surgeries, and typically more. The use of the compositions of the present disclosure in combination with surgical revision can greatly reduce this problem. The beneficial effect can particularly be seen in relation to the volume of scar tissue that forms outside of the normal skin boundary layer. Evaluation of scar volume is particularly discussed in Example 12. In specific embodiments, the scar tissue volume present 12 months after revision surgery with application of the present matrix composition relative to the scar tissue volume prior to revision surgery is about 15% or less. In other words, the revision methods described herein can reduce external scar volume by 85% or greater. In further embodiments, the relative external scar volume 12 months after revision surgery can be 10% or less, 5% or less, or 2% or less.

The disclosed use of the composition likewise can prevent or reduce recurrence of keloid formation such that treatment results in no measurable, raised scar tissue at a time of 12 months after treatment. For example, a reduced rate of recurrence at 12 months post-treatment can be 20% or less, 15% or less, 10% or less, or 5% or less of treated patients experiencing no measurable, raised scar tissue.

Treatments and uses of the compositions according to the disclosure further can be characterized in relation to effects of scarring. Thus, not only can the use and application of the compositions prevent or reduce scarring, including hypertrophic scarring and keloid formation, the use and application of the compositions can prevent or reduce an effect of scarring and thus prevent or reduce patient discomfort and/or dissatisfaction associated with any scar tissue formed. For example, effects of scars that can be prevented or reduced include one or more of pain, itching, discoloration of the scar tissue and/or surrounding tissue, abnormal stiffness of the scar tissue or surrounding tissue relative to the subject's normal skin tissue, abnormal thickness of the scar tissue or surrounding tissue relative to the subject's normal skin tissue, and surface irregularity of the scar tissue or surrounding tissue (e.g., roughness and unevenness).

It is believed that the foregoing discussion in combination with the appended examples meets the necessary disclosure requirements for the preparation of a phase-controllable matrix composition that is useful in treating wound sites (chronic, traumatic, or surgical) to reduce or prevent post-surgical scarring, hypertrophic scarring, burn scarring, and/or keloid formation. Further exemplary materials and methods of preparing compositions that can be useful in combination with the present disclosure are provided in the following: U.S. Pat. No. 5,824,331; U.S. Pat. No. 6,231,881; U.S. Pat. No. 6,261,587; U.S. Pat. No. 6,352,707; U.S. Pat. No. 6,713,079; U.S. Pat. No. 6,992,062; U.S. Pat. No. 6,730,315; U.S. Pat. No. 7,303,814; U.S. Pat. No. 7,700,660; U.S. Pat. No. 7,799,767; U.S. Pat. No. 8,053,423; US Patent Publication No. 2008/0145404; US Patent Publication No. 2008/0145404; US Patent Publication No. 2008/0199508; US Patent Publication No. 2009/0123547; and US Patent Publication No. 2009/0124552. The disclosures of all of the preceding documents are incorporated herein by reference in their entireties.

EXAMPLES

The present invention is more fully illustrated by the following examples, which are set forth to illustrate the present invention and are not to be construed as limiting thereof.

Example 1

Preparation of Gelatin/Dextran Composition

A composition according one embodiment of the present disclosure was prepared by sequentially adding the liquid and powdered raw materials (Table 1) at specific time points at elevated temperatures, while mixed to maintain a liquid, homogeneous state. The solution was then sterile filtered, aseptically dispensed into vials, sealed, and stored at refrigerated temperatures.

TABLE 1

| Component | Concentration |
| --- | --- |
| Gelatin—Type-A porcine gelatin 100,000 Da Avg. MW | 120 mg/ml |
| Dextran 500,000 Da Avg. MW | 50 mg/ml |
| Medium 199 Custom Formulation C5866 | 0.83 ml/ml |
| L-Glutamic Acid, Monosodium Salt, N.F. | 3.74 mg/ml |
| L-Arginine Monohydrochloride, USP | 3.16 mg/ml |
| Edetate Disodium, USP | 1.31 mg/ml |
| L-Lysine Acetate, USP | 1.03 mg/ml |
| L-Cysteine HCl Injection, USP | 0.13 mg/ml |
| Zinc Sulfate, USP | 0.005 mg/ml |
| L-Alanyl-L-Glutamine | 0.002 mg/ml |
| 50% Dextrose Injection, USP | 0.50 mg/ml |
| Hydrochloric Acid, USP | As needed to adjust pH |
| Sodium Hydroxide, NF | As needed to adjust pH |
| Sterile Water for Injection, USP | As needed to adjust osmolality |

The dextrose and Medium 199 were measured and transferred to a pre-heated, water-jacketed (50° C.) glass vessel and mixed using a stir bar. The mixture was allowed to equilibrate to 50° C. after which L-Cysteine, L-Alanyl-L-Glutamine, L-Glutamic Acid, L-Lysine, and EDTA Disodium were dispensed into the vessel with Medium 199. After an equilibration time, dextran powder was added, and the components were mixed. Once the dextran appeared to be in solution, gelatin was added to the vessel and allowed to dissolve. Once the gelatin appeared to be in solution, pH was adjusted to 7.45+/−0.05. After equilibration from the pH adjustment, the remaining L-Glutamic Acid, Arginine, and L-Cysteine were stirred into the solution along with the Zinc Sulfate. The total mixing time was approximately 2 hours.

After equilibration at 50° C., the solution was filter sterilized by pumping the solution from the mixing vessel through a heated, 0.2 µm positively charged, pharmaceutical grade nylon filter into a 40° C. stirring vessel for queuing prior to aseptic filling. Filtration was performed in approximately 30 minutes. After the solution was filtered, it was aseptically dispensed into 12 ml aliquots into vials while it continued to be mixed while maintained at 40° C. The vials were subsequently stoppered, sealed, crimped, visually inspected, labeled, and then stored under refrigeration (2-8° C.). The production yielded approximately 150 vials. The dispensing of the composition was performed in approximately one hour.

Example 2

Preparation of Gelatin/Dextran Composition with Phosphate Buffer

Using the processing methods described in Example 1, the composition was prepared by sequentially adding the liquid and powdered raw materials at elevated temperatures while mixed to maintain a liquid, homogeneous state. The solution was then sterile filtered and aseptically dispensed. The composition was prepared by first placing 2,282 ml of phosphate buffered saline (PBS) into a pre-heated, water-jacketed (50° C.) glass vessel and mixed using a stir bar. The mixture was allowed to equilibrate to 50° C. after which the 375 µl of L-Cysteine, 6.9 ml of L-Glutamic Acid, 13.8 ml of L-Lysine, and 24.2 ml of EDTA Disodium were dispensed into the vessel with PBS. After an equilibration time, 137.5 grams of dextran powder was added and the components were mixed. Once the dextran appeared to be in solution, 330 grams of gelatin was added to the vessel and allowed to dissolve. Once the gelatin appeared to be in solution, 10% sodium hydroxide was added to adjust the pH to 7.45+/−0.05. After equilibration from the pH adjustment, 20.6 ml of L-Glutamic Acid, 20.6 ml of Arginine, 13.8 ml of Zinc Sulfate, and 6.5 ml of L-Cysteine were stirred into the solution. The vials were subsequently stoppered, sealed, crimped, visually inspected, labeled, and then stored under refrigeration (2-8° C.). The total mixing time was approximately 2 hours.

Example 3

Thermal Properties of Composition

The thermal properties of the compositions from Example 1 and Example 2 were examined by differential scanning calorimetry (DSC). Samples of the compositions from Examples 1 and 2 were incubated for 60 minutes at 5° C. and then subjected to DSC testing at a scan rate of 5° C. per minute, starting from 5° C. to an ending temperature of 45° C. The thermal properties were evaluated from the representative thermagrams and enthalpy of thermal transitions. A melt transition of the solid composition to a liquid was observed, with a transition peak ranging from 35 to 37° C. A representative thermogram for the is shown in FIG. 1.

Example 4

Flowability/Injectability of Composition

A composition of 60% gelatin and 40% dextran was solubilized to a final solids concentration of 0.2 g/ml in Tris buffered saline (TBS) heated to 50° C. The resulting composition was divided into 4 ml samples and placed in 20 ml vials, and the vials with the samples were stored at 4° C. To evaluate flowability, a vial of the composition was removed from storage and placed at room temperature. The vial was then placed in a heater (Lab-line Multiblock Heater) at 39° C. and monitored until the composition transitioned from a solid to a flowable liquid. The liquid composition was placed into a 1 ml syringe and attached to a fluid dispensing system (1500 XL, Nordson/EFD) set to a plunger force of 5 N, the recommended force for a 1 ml syringe by the international guidance for sterile hypodermic syringes for single use (see, ISO 7886-1). A 25 gauge needle (0.26 mm nominal inner diameter) of approximately 16 mm (⅝ inch) length was attached and the time for passage of 1 ml of composition through the needle was recorded. Injection through the needle was carried out at a temperature of about 39° C. The composition met the conditions for administration by injection through a fine gauge needle according to ISO 7886-1, which specifies requirements (including performance) for sterile, single-use hypodermic syringes made of plastic materials and intended for the aspiration of fluids or for the injection of fluids immediately after filling.

To examine the solids content of the composition to evaluate suitability for injection through a small gauge needle, the total polymer content of dextran and gelatin in the composition was varied as presented in Table 2. The polymers were solubilized in 10 ml of HEPES buffered saline (0.01M HEPES, 0.138 M NaCl, and 0.0027 M KCl) with slow mixing in 15 ml conical tubes at 50° C.

TABLE 2

| Total Polymer (mg/mL) | Gelatin (mg/mL) | Dextran (mg/mL) |
|---|---|---|
| 190 | 120 | 70 |
| 304 | 192 | 112 |
| 380 | 240 | 140 |
| 427.5 | 270 | 157.5 |
| 475 | 300 | 175 |

After preparation the samples were cooled. Using the testing methods described above, the samples were placed in a 39° C. heating block and 1 ml was injected through 25 gauge and 23 gauge needles that were one inch long (22.5 mm). Each sample was tested a minimum of three times through each needle size for injection rate. If a minimum of 0.5 ml was not able to be injected through the needle, the test was unsuccessful, and the sample continued to be heated until successfully injected. The results of the injection testing are presented in Table 3.

TABLE 3

| Total Polymer (mg/mL) | Approximate Melt Time (min) | 23 G Avg. Rate (µL/sec) | 25 G Avg. Rate (µL/sec) |
|---|---|---|---|
| 190 | 8 | 63 | 29 |
| 304 | 10 | 15.4 | 5.7 |
| 380 | 8 | 7.6 | 2.3 |
| 427.5 | 14 | 3.5 | unable to inject |
| 475 | 18 | 1.6 | unable to inject |

The formulations tested for injectability were characterized for viscosity to determine the maximum viscosity to allow injection. Sample formulations using the same ratio of gelatin to dextran tested for injectability were prepared at various total polymer content in HEPES buffered saline as previously described. The samples were preconditioned at 50° C. and loaded into a Rheometrics Scientific RFSII Rheometer with Couette Geometry for testing. Multiple measurements were made with freshly loaded samples at 39° C. until viscosity stabilized to equilibrium measurement values. A shear rate range up to 1000 s$^{-1}$ was tested; however, the shear rate range for each sample was adjusted to the torque range of the rheometer. Shear rate range was reduced for high concentration samples.

The samples from 190 to 380 mg/mL total polymer demonstrated Newtonian viscosity response. The higher concentration samples demonstrated slight non-linear viscosity response but were suitable for characterization by standard linear regression analysis. The viscosity results are summarized in Table 4. Formulation viscosity greater than 0.4565 Pa·s was not suitable for injection through a 25 gauge needle. Viscosity of up to 1.1618 Pa·s was injectable through a 23 gauge needle.

TABLE 4

| Total Polymer (mg/mL) | Viscosity Avg (Pa-s) | Viscosity Std Dev (Pa-s) |
|---|---|---|
| 190 | 0.0598 | 0.00045 |
| 285 | 0.1983 | 0.03579 |
| 380 | 0.4565 | 0.02748 |
| 427.5 | 0.7514 | 0.03334 |
| 475 | 1.1618 | 0.02666 |

Example 5

Fibronectin Binding Activity of Composition

The composition of Example 1 was evaluated in relation to fibronectin binding activity of the gelatin. The assay followed a direct ELISA binding format where test material was immobilized on well surfaces of a microtiter plate to bind fluoresceinated human plasma fibronectin to enable direct measurement of fluorescence of the captured tagged fibronectin. In this assay, the composition of Example 1 was completely melted (by incubation at 39° C. for 30 minutes), and diluted with pH 9.6 buffer to yield final gelatin concentration in the range of 1 to 10 µg/mL to coat wells of a high-binding opaque 96-well plate, optimal for fluorescence measurement. The gelatin used in the composition was immobilized irreversibly onto the well surfaces by incubation of the plate at 39° C. for one hour. Excess unbound materials and buffers were removed, and the plate was washed three times with PBS (Phosphate Buffered Saline) containing 1M NaCl (Wash Buffer). Nonspecific binding sites were blocked by 3% milk in PBS (Blocker) for 30 minutes at room temperature. Excess buffer was removed and the plate was washed 3 times with Wash Buffer as performed previously. Human plasma fibronectin, conjugated with 1 to 5 fluorescein molecules per fibronectin molecule, diluted with Blocker to a final concentration of 45 µg/mL, was then added to the plate wells. The plate was covered and rotated gently at room temperature for 2 hrs to allow maximal binding in the dark. Excess fluoresceinated fibronectin was removed, and the plate was washed 3 times with Wash Buffer as performed previously. PBS (100 µL) was added to each well, and fluorescence was recorded by a plate reader, using excitation wavelength at 485 nm and emission wavelength at 530 nm Plates were read several times, and the data averaged.

Both samples and standards were measured in duplicates. The gelatin raw material used in the composition was tested at seven concentrations (see Table 5) to generate a standard curve. The composition samples were tested at four diluted concentrations. Concentrations of gelatins in each sample were determined from the range of standards by linear regression.

TABLE 5

| Gelatin (μg) | Average Relative Fluoresence Units, background corrected |
|---|---|
| 1 | 7.24 |
| 0.8 | 6.75 |
| 0.5 | 5.57 |
| 0.4 | 4.59 |
| 0.25 | 2.86 |
| 0.2 | 2.05 |
| 0.125 | 0.97 |
| 0 | 0 |

In order to compare the fibronectin binding content of the composition, the protein content was also measured and used to normalize the amount of fibronectin binding sites of each sample. Protein concentration was measured by the colorimetric Bicinchoninic Acid (BCA) assay (Pierce Biochemical Micro BCA protein assay kit, #23235) according to the manufacturer's instructions. Briefly, gelatin raw material was prepared in 2-fold diluted concentrations of 1.56 to 100 μg/mL with PBS (pH 7.4, Sigma P5368). Samples (typically at 5 mg/mL in PBS starting concentrations) were diluted to 25 to 50 μg/mL in PBS (5 to 10 μL of 0.5 mg/mL protein and 90 to 95 μL PBS). The reactions were carried out in a clear 96-well plate, optimal for UV/Vis absorbance measurements, by mixing 100 μL of sample with 100 μL BCA Working Reagent (25:24:1, Reagent MA:MB:MC) and allowing the plate to rotate gently in a 37 to 39° C. oven for 15 to 30 min to develop the purple color indicating protein content. The absorbance at 562 nm of each reaction was then recorded by a spectrophotometric plate reader (Spectramax M5, Molecular Devices). Each concentration of both samples and standards was done in duplicates and averaged.

Table 6 shows the measured concentrations of fibronectin binding sites, normalized to the protein concentration by comparing the ratio of fibronectin to mg/mL protein, of low numbered and high numbered vials of the composition as prepared in Example 1. The samples were initially melted at 39° C. (for 1 hr) and diluted to 5 mg/mL with PBS. The samples were then melted at 39° C. for 30 min to completely dissolve the gelatin before they were diluted further to 0.5 mg/mL with PBS for both fibronectin binding and BCA protein assays.

TABLE 6

| Vial # | Fibronectin Binding/ Protein (nmol/mg) |
|---|---|
| #8 | 5.66 |
| #144 | 5.85 |

The test results show that the gelatin raw material demonstrates significant fibronectin binding activity. The fibronectin binding property is retained in the composition of the present disclosure from both a vial collected early during production (vial #8) as well as a vial collected near the end of production (#144).

Example 6

Physical Properties of Composition

A dissolution assay was used to measure composition resistance to loss of integrity from solubilization (dissolution) in a physiological solution as a measure of residence time in a wound. This assay was based on standard dissolution testing per the United States Pharmacopeia (USP) XXIII, 1995:1791-1793, modified for the testing of small volumes in a simulated dermal environment. The assay measured the total time (in minutes) for the complete dissolution of a sample disk of the composition at skin temperature 34° C., under a set of defined conditions: one disk per 3 mL PBS (pH 7.4) in a 20-mL vial, rotating gently (200-250 rpm) in a 34° C. oven.

To form the cast disks, vials of the composition from Example 1 were melted at 35° C. for 1.5 hours, mixed by inverting while rotating vials 10-15 times. The melted composition was removed in 1 mL aliquots to fill 6-12 circular wells (disks of 8 mm diameter and 1.5 mm height) of a polypropylene mold, tightly sealed to a flat metal plate by a thin rubber mat. The disks were allowed to cool and form a gel at room temperature for 30 minutes before they were removed from the mold, and stored in pre-weighed capped tubes. The disk weight, typical range of 70-100 mg, was determined for identification. Disks were allowed to set at room temperature for a total of 1-2 hours before they were tested. For each vial of the composition, 3 disks with minimal air bubbles were chosen for the complete dissolution test. Each disk was added to 3 mL PBS, pre-warmed at 34° C., and placed on a rotating platform in 34° C. oven. For each test, the vials were monitored simultaneously by visual inspection, every 5-15 minutes. The samples were observed to be an integral disk that slowly became smaller during the test as the material at the surface was solubilized. The observation of samples was done quickly to minimize the temperature change in these samples. The time for complete dissolution of each disk was recorded (see FIG. 2).

The compressive strength of the composition was also examined by mechanical testing of cylindrical test samples cast from the composition. The testing was based on compressional mechanical testing as described in ASTM D575-91 (2007) Test Methods for Rubber Properties in Compression, modified for the testing of small hydrogel samples. To form cast sample cylinders, vials of the composition were melted at 35° C. for 1.5 hours and mixed by inverting while rotating vials 10-15 times. The melted composition was removed in 1-mL aliquots to completely fill, but not overfill, each circular well (cylinder of 1 cm diameter and 1 cm height) of a 15-well Delrin mold, tightly sealed to a flat metal plate by a thin rubber mat. Typically, 5 cylinders were cast from each vial.

Figure 2:
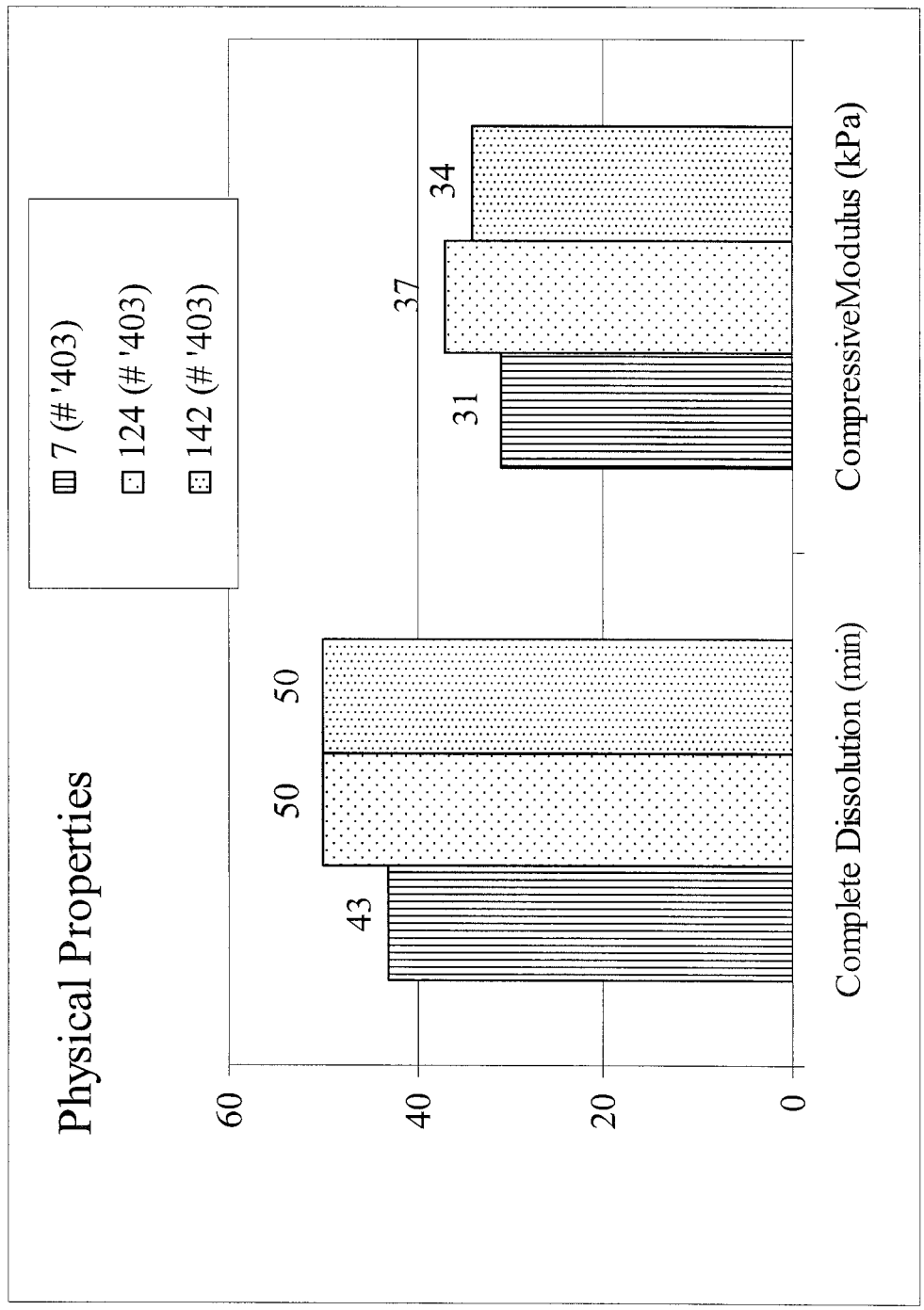
FIG. 2 is a graph showing physical properties of compositions according to exemplary embodiments of the present disclosure.

The molds were allowed to set at room temperature for 1.5 hour, and the samples gently removed from the mold. Cylinders were weighed (range=0.7-1 g) for identification, and allowed to set at room temperature for a total of 1-4 hours before they were tested. Each cylinder was then placed in a plastic cylindrical holder (1.5 cm diameter and 1.5 cm height), and was compressed by a flat pin (with head 1 cm diameter and 10 mm height), clamped tightly to the transducer of a mechanical tester (Instron Model 5542). Compressive modulus was measured by the Instron, using a 5 Newton load cell, at a speed of 3 mm/min. The modulus value for compressing each cylinder, calculated by the Instron was reported as the automatic modulus value (in kPa units). For each vial, 3-4 cylinders were measured. For each cylinder, 3-4 consecutive consistent values were averaged. Maximal compressive load (gf) and compressive stress at maximal compressive load (kPa) values were also measured by the Instron instrument. Testing results from vials of composition of Example 1 demonstrate greater physical properties from the high numbered vials produced later during the batch process, as indicated in FIG. 2.

Example 7

Stoichiometry of Composition

To examine the suitable formulation stoichiometry, various amounts of gelatin (Gelita USA, Inc., Type A porcine gelatin) and dextran (Sigma Aldrich, Dextran 500,000 MW) were weighed, combined in a 5 mL snap-cap tubes, and 2 mL PBS, pH 7.4 was added. Samples with total polymer weight (gelatin plus dextran) of 200 mg/ml and 230 mg/ml were prepared and tested. The samples were vortex mixed briefly before incubation overnight. All samples were rotated gently at 8 rpm overnight in a 50° C. oven for approximately 19 hours. At that time the samples represented a homogenous, flowable composition. By pouring the compositions into molds used for the dissolution testing, 6-9 disks were cast for each composition, and allowed to set at room temperature for 30 minutes. The de-molded disks (three for each composition) were allowed to set for another 1.5 hours at room temperature. The sample disks were tested in the dissolution assay for physical integrity as described in Example 6 using three disk samples for each test composition, with each disk exposed to 3 mL PBS while gently rotating at 34° C. The disk samples were monitored every 15 minutes for physical integrity.

The dissolution results in Table 7 indicates a lack of physical integrity for samples with 60 weight percent gelatin or less for both polymer concentrations. Samples with greater than 60 weight percent gelatin showed approximately the same amount of dissolution resistance when tested at physiological pH and ionic strength.

TABLE 7

| Gelatin (mg/mL) | Dextran (mg/mL) | Wt % Gelatin | Wt % Dex | Dissolution Time (min) |
|---|---|---|---|---|
| 120 | 80 | 60% | 40% | 0.000 |
| 140 | 60 | 70% | 30% | 55.000 |
| 160 | 40 | 80% | 20% | 60.000 |
| 180 | 20 | 90% | 10% | 60.000 |
| 200 | 0 | 100% | 0% | 60.000 |
| 138 | 92 | 60% | 40% | 0.000 |
| 161 | 69 | 70% | 30% | 65.000 |
| 184 | 46 | 80% | 20% | 55.000 |
| 207 | 23 | 90% | 10% | 66.667 |
| 230 | 0 | 100% | 0% | 60.000 |

Figure 3:
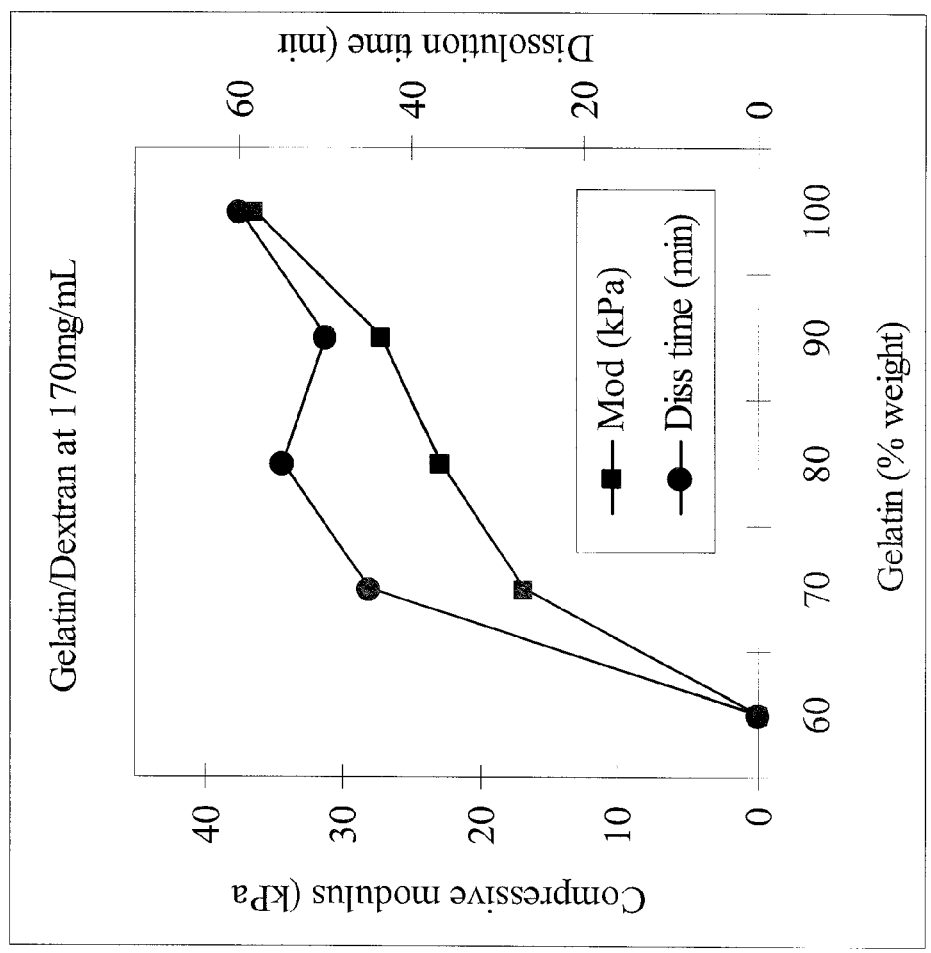
FIG. 3 is a graph showing physical properties of compositions according to further embodiments of the present disclosure relative to the gelatin concentration of the compositions.

In a second experiment, the gelatin and dextran of the previous experiment were formulated in PBS at a concentration of 170 mg/ml total polymer with 60%, 70%, 80%, 90% and 100% gelatin. The five different ratios of gelatin to dextran formulations were heated to liquefy the material and cast disk samples for characterization of physical properties using the methods of Example 6. The results demonstrated dissolution resistance of the formulations with greater than 60% gelatin, similar to the previous experiment. The compressive testing of the formulations also demonstrated significant increase in physical properties of the formulations with greater than 60% gelatin. The test results are illustrated in FIG. 3.

Example 8

Lyophilization of Composition and Reconstitution for Use

The composition of Example 2 was frozen and lyophilized to dryness. The composition was frozen to approximately −30° C. at a cooling rate of approximately 0.05° C./min and held at −30° C. for approximately 12 hours. A vacuum was applied to the frozen composition at −30° C. for approximately 24 hours. Thereafter, the temperature was incrementally increased to approximately −10° C. at a rate of approximately 0.25° C./min. The composition was then held under vacuum at approximately −10° C. for at least 12 hours before the temperature was further increased to approximately 20° C. at a rate of approximately 0.05° C./min. The lyophilized composition was then weighed and placed into vials.

Vials containing the lyophilized composition were reconstituted with deionized water to form a flowable composition suitable for administration to a wound. One gram of lyophilized composition was mixed with 5 ml water in a vial to give a final concentration of 0.2 g/ml. The vials were heated at 39° C. for 1 hour and mixed by vortexing at 15 minutes and 30 minutes. The result was a flowable, liquid composition suitable for injection into dermal and subdermal tissues as discussed above.

The lyophilized composition was assayed for fibronectin binding, dissolution time, and compressive modulus using the methods described in Examples 5 and 6. The reconstituted composition demonstrated fibronectin binding in the range of 5.13 to 5.88 nmol/mg, dissolution time in the range of 30 to 45 minutes, and compressive modulus in the range of 17 to 29 kPa. When 1% glycerol and 0.1% Tween 20 was added to the reconstitution fluid, the reconstituted composition demonstrated a dissolution time of 33 minutes and a compressive modulus of 34 kPa. When 0.15M NaCl and 1% Tween 20 was added to the reconstitution fluid, the reconstituted composition demonstrated a dissolution time of 30 minutes and a compressive modulus of 33 kPa.

Example 9

Reconstitution of Lyophilized Composition for Injection into Wounds/Tissues

The reconstitution of the composition according to Example 8 was examined under various conditions. Vials of the lyophilized composition were mixed with 5 ml of reconstitution fluid preheated to 39° C. to produce a solids content of 0.2 g/ml. The vials were placed in a 39° C. block heater and observed after 5 minutes and vortex mixed. The vials were visually examined subsequently every 1 to 2 minutes and vortex mixed until a flowable, uniform liquid was observed. The reconstituted composition was then tested for ability to flow by injection with a 1 ml syringe through a 25 gauge needle under the conditions described in Example 4.

The liquid composition was considered injectable if 0.5 ml of the fluid was able to be injected. If clogging of the needle during injection of a volume less than 0.5 ml was observed, the vial was continued to be heated and mixed until successful injection. The results are summarized in Table 8, wherein component percentages are provided in weight % unless otherwise stated.

TABLE 8

| Vial # | Reconstitution Fluid | Time to Reconsitute (min) | Injection Rate at 5N (μL/sec) |
|---|---|---|---|
| 1 | Deionized Water | 14 | 21 |
| 2 | Deionized Water, 1% glycerol | 13 | 43 |

TABLE 8-continued

| Vial # | Reconstitution Fluid | Time to Reconstitute (min) | Injection Rate at 5N (µL/sec) |
|---|---|---|---|
| 3 | Deionized Water, 1% Tween 20 | 19 | 18 |
| 4 | Deionized Water, 0.15M NaCl, 1% Tween 20 | 9.5 | 33 |
| 5 | Deionized Water, 1% Glycerol, 0.1% Tween 20 | 9.3 | 32 |
| 6 | Deionized Water, 1% Dextrose, 0.025% Tween 20 | 12 | 32 |

The results demonstrate the ability of a lyophilized composition of the product to be reconstituted into a fluid that is injectable by a fine gauge needle. Reconstitution additives, including hygroscopic excipients, bulking agents, and surfactants, demonstrated the ability to reduce the time to reconstitute the lyophilized composition into an injectable fluid and/or reduce the time to inject the composition under a standard 5 N injection force.

Example 10

Tissue Reaction of Composition in Animal Dermal Model

Samples of the composition of Example 1 were heated at 38° C. to form a flowable liquid composition suitable for injection. The composition was injected into the abdominal dermis of forty-four anesthetized adult female Sprague-Dawley rats. The animals were monitored daily until necropsy of four animals each at 1, 3, 6, 9, 12, 15, 18, 21, 24, 27 and 28 days post injection. Tissue samples were harvested at the site of injection and histologically prepared. H&E histopathology of the tissue from the injection sites were examined for cellular reaction and presence of the injected composition.

Histopathology demonstrated the composition to reside in the subdermal space as a single mass of lightly staining material with thin fibrils of eosinophilic fibers uniformly dispersed throughout. The composition showed mild infiltration of polymorphonuclear leukocytes (PMNs) into the composition and surrounding tissue at day 1, with increased amount of cellular infiltration at day 3. The amount of composition appeared decreased at day 3. The 6 day implants demonstrated progressively less of the composition. The 9 day implants showed no composition present in 2 of the animals, with a corresponding decrease in the presence of inflammatory cells. Small amounts of the composition were evident in one animal at tissues from day 12, day 15 and 18. No evidence of the composition was found at day 21 tissues. Small amounts of the composition were found in tissues from two animals at day 24. No evidence of the composition was found in tissues from day 27 and day 28. After the implant material was no longer evident, the injection site tissues demonstrated minimal presence of PMNs, no significant presence of macrophages and no evidence of new collagen deposition or scar formation, demonstrating a very benign tissue reaction. Subsequent histopathology determined that there was no collagen deposition or angiogenesis associated with the composition.

Example 11

Administration of Composition to Treat Surgical Wounds

One hundred female subjects between the ages of 18 and 60 years of age undergoing laparotomy or laparoscopy gynecologic procedures were recruited to participate in a prospective randomized, same-scar controlled trial to evaluate the improvement in wound healing by assessing the signs and symptoms of scar formation following a single treatment with the composition of Example 1. Ninety subjects were treated by injection and ten subjects were treated via a catheter.

The subjects' surgical incisions were divided in half, with one half randomly assigned to "treatment" with the composition and the other half assigned to "control" (no treatment) just prior to closing the incision with sutures. Patients returned for follow-up visits through 12 months post-treatment for assessment of the surgical incision halves.

At the time of wound closure in the ninety subjects treated by injection, the composition was heated at 39° C. (+/−2° C.) to form a flowable, injectable liquid. The physician used a syringe and an 18-25 gauge needle to inject the composition into the wound margins. The needle was inserted deep enough into the dermal-subdermal interface and as parallel as possible to the incision wound edge. The needle track and surrounding tissue was infused with sufficient amounts of the composition such that the area surrounding and including the needle track was supplied with approximately 1-2 mL of the composition per 2.5 cm of the wound margin. Effectiveness was evaluated with a validated scar assessment scale using observer (surgeon) and patient assessments of scar characteristics—i.e., the Anchored Visual Analog Scales (AVAS), which were based on the previously validated Visual Analog Scale (VAS), and the Patient and Observer Scar Assessment Scale (POSAS).

A standard VAS evaluation uses a 100 mm horizontal visual analog cosmetic scale marked "worst possible scar" at the left end and "best possible scar" at the right end. The evaluator was asked to mark along the horizontal scale indicating the overall aesthetic appearance of the scar. Numeric scores were calculated by measuring horizontal distance from the low end of the scale to the evaluator's mark and rounding to the nearest millimeter. The AVAS scale uses a horizontal visual analog cosmetic scale that allows the evaluator to select the worst scar half as an anchor for the left end of the scale while using normal skin at the right end of the scale. The evaluator was asked to mark along the horizontal scale indicating the overall aesthetic appearance of the better scar half between the two ends. Numeric scores were calculated by measuring horizontal distance from the low end of the scale to the evaluator's mark and rounding to the nearest millimeter.

The observer and patient AVAS scores through 12 months were analyzed using generalized estimating equations (GEE), which is a method for analyzing longitudinal data that takes into account the expected correlation among observations for the same subject. The AVAS analyses were performed assuming an autoregressive structure. The GEE analyses were used to obtain an estimated mean difference between treatments (control side-treated side) overall and for the individual characteristics for the AVAS scores, and to perform a two-sided normal approximation test for statistical significance.

The ninety subjects treated by injection of the composition were evaluated by a surgeon observer and the treated subject using the anchored visual analog scale (AVAS). After treatment of the first 30 subjects, the protocol was amended to include the AVAS scale. For the first 30 subjects enrolled, the AVAS scores were only collected from the observer and patient at the 9 and 12 month follow-up visits. The next 60 subjects enrolled had AVAS data collected from the observer and patient at all follow-up time points. When evaluating AVAS for treated versus control, the overall estimated AVAS difference for the Observer and Patient evaluation through 12 months were 7.49 mm (p=0.0018) and 9.86 mm (p=0.0009), respectively, in favor of the treated side. The results for the Observer and Patient AVAS are presented in Table 9.

TABLE 9

Summary of treatment effect estimate and P-value by GEE (Observer and Patient AVAS Scores) through 12 months (n = 90)

| Parameter | Estimate | p-value |
| --- | --- | --- |
| Observer AVAS | 7.4939 | 0.0018 |
| Patient AVAS | 9.8605 | 0.0009 |

The effectiveness of the composition was also evaluated with the validated POSAS scar assessment scale by GEE, as noted above, using observer (physician/investigator) and patient live assessments of scar characteristics. The observer scale of the POSAS consists of five wound healing characteristics which are scored numerically on a scale of 1-10, whereby 1 is the best score and 10 is the worst. The total score of the observer scale consists of adding the scores of each of the five items (range, 5 to 50). The lowest score (5) reflects normal skin. The results are shown below in Table 10 and Table 11. When evaluating Observer POSAS scores for treated versus control, the overall estimated difference through 12 months was 0.98 (p=0.0051), in favor of the treated side and the estimated POSAS differences for the individual Observer-evaluated characteristics ranged from 0.20 to 0.26 and were all significantly in favor of the treated scar half. When evaluating Patient POSAS scores for treated versus control, the overall estimated difference through 12 months was 1.19 (p=0.0012) in favor of the treated side and the estimated POSAS differences for the individual Patient-evaluated characteristics ranged from 0.09 to 0.36 and were all significantly in favor of the treated scar half

TABLE 10

Observer POSAS Score Through 12 months (n = 90)

| Characteristic | Estimate | p-value |
| --- | --- | --- |
| Vascularization | 0.2598 | 0.0005 |
| Pigmentation | 0.2453 | 0.0018 |
| Thickness | 0.1996 | 0.0042 |
| Relief | 0.2275 | <0.0001 |
| Pliability | 0.2209 | <0.0001 |
| Overall | 0.9839 | 0.0051 |

TABLE 11

Subject POSAS Score Through 12 months (n = 90)

| Parameter | Estimate | p-value |
| --- | --- | --- |
| Pain | 0.0918 | 0.0375 |
| Itching | 0.1369 | 0.0248 |
| Color | 0.2700 | 0.0018 |

TABLE 11-continued

Subject POSAS Score Through 12 months (n = 90)

| Parameter | Estimate | p-value |
| --- | --- | --- |
| Stiffness | 0.3581 | <0.0001 |
| Thickness | 0.3261 | 0.0002 |
| Irregularity | 0.1612 | 0.0126 |
| Overall | 1.1905 | 0.0012 |

Example 12

Administration of Composition for Surgical Revision of Keloids

A study was performed to evaluate the use of the composition in the reduction of the volume, appearance, and/or symptoms associated with keloid scarring in subjects undergoing surgical revision of keloid scars by excision of the keloid tissue as compared to recurrence rates reported in contemporary literature.

Nineteen subjects with 26 ear keloids were enrolled in the study. Keloids on the ears of the study subjects were surgically removed and the wound margins of the incision were identified. The composition of Example 1 was heated at 39° C. (+/−2° C.) for a minimum of 60 minutes prior to injection. A 25 gauge needle was inserted deep enough into tissue to be in the dermal/subdermal interface and as parallel as possible to the incision wound edge. The investigator injected the composition such that it was dispersed into the infusion track and into the surrounding tissue as the needle was withdrawn. The needle track and surrounding tissue in the wound margins were infused with sufficient amounts of composition, an average of 1.48 ml per every 2.5 cm increment of the incision length on each side of the wound margin. The investigator was also guided by visual and tactile feedback during the injection process such as skin tension caused by the injection, ease of flow of the composition from the needle, blanching of the tissue, and the physical ability of the tissue to contain the composition. All incision locations (i.e., right ear, left ear and/or both ears) were closed in the same manner.

A protocol for keloid volume measurement using impressions with dental alginate was used to measure lesion size volume. The volume of the keloid was measured by filling the alginate impression with water and weighing the volume on a calibrated scale. This allowed a numerical value to be obtained for the volume of the lesion. Impressions were to be made of only those lesions amenable to alginate impressions. An alginate impression was made and volumes were calculated for each subject at baseline. At the 12 month follow-up visits, five ears (19.2%) were identified as having recurrences based on clinical examination. Molds were cast for each ear. The pre-surgical volumes and the 12 month volumes of the molds are included in Table 12 below. Additionally, the percentage of the pre-surgical volume has been calculated for each of the 12 month molds. Of the five recurrences from treatment with the composition, two of the recurrences demonstrated clinically significant lesion size of 5% or greater at 12 months.

TABLE 12

Lesion Volume as Measured by Alginate Mold

| Subject | Pre-surgical Volume | 12 Month Volume | % of Pre-surgical Volume |
|---|---|---|---|
| 08-02-TS | 3.867 gm | 0.18 gm | 4.7% |
| 08-09-KA-R | 7.641 gm | 0.040 gm | 0.5% |
| 08-11-TO-R | 2.542 gm | 0.365 gm | 14.4% |
| 08-11-TO-L | 2.664 gm | 0.345 gm | 13.0% |
| 08-18-DS | 3.138 gm | 0.027 gm | 0.9% |

The literature specific to keloid recurrence following surgical excision indicates that concomitant therapy (e.g., surgical excision/corticosteroid injections) has become the standard of care. Included in Table 13 below is the literature most relevant to keloid recurrence following surgical excision alone.

TABLE 13

| Study | Year | Excision | # Patients | % of Recurrence |
|---|---|---|---|---|
| Nason | 1942 | Scalpel | 12 | 83% |
| Arnold | 1959 | Scalpel | 14 | 86% |
| Conway | 1960 | Scalpel | 28 | 45% |
| Cosman | 1961 | Scalpel | 25 | 54% |
| Cosman | 1972 | Scalpel | 7 | 57% |
| Cosman | 1974 | Scalpel | 20 | 73% |
| Ramakrishnan | 1974 | Scalpel | 108 | 80% |
| Oluwasanmi | 1974 | Scalpel | 41 | 93% |
| Apfelberg | 1989 | Laser | 9 | 89% |
| Stern | 1989 | Laser | 23 | 74% |
| Berman | 1997 | Scalpel | 43 | 51% |
| Kim | 2004 | Scalpel | 9 | 44% |

Recurrence was documented in the literature between 44-93%. A study by Berman et al. (Berman B., Flores F. "Recurrence rates of excised keloids treated with postoperative triamcinolone acetonide injections or interferon alfa-2b injections", *J AM Acad Dermatol.* 1997; 37:755-7) has been deemed to be the best contemporary literature comparator, as the publication includes a data set of a significant number of subjects. When considering surgical excision of earlobe keloids specifically, Berman et al. studied 43 patients undergoing surgical excision alone (86% with earlobe or ear helix keloids), 51.2% of the keloids recurred in an average of 6.5 months. Analyses were performed comparing the treatment results using the composition to results from Berman et al. (1997).

Using a 2×2 contingency table, the treatment results using the composition of the present disclosure (as described above) were compared to the Berman et al. publication. Analysis using Fisher's exact test demonstrated a two tailed p value of 0.011, indicating a statistically significant difference. The composition was found to be significantly superior to reported surgical excision alone for preventing keloid recurrence when evaluated at 12 months. The composition demonstrated the ability to prevent and minimize keloid recurrence when administered by injection with a small gauge needle to dermal and subdermal tissues during keloid revision surgery.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed herein and that modifications and other embodiments are intended to be included within the scope of the appended claims. Although specific terms are employed herein, they are used in a generic and descriptive sense only and not for purposes of limitation.

The invention claimed is:

1. A method for the revision of a cutaneous keloid or hypertrophic scar, the method comprising:
    excising at least a portion of the keloid or hypertrophic scar tissue so as to form an excision site; and
    applying a hydrogel matrix composition to the dermal or subdermal tissue in or around the excision site;
    wherein the hydrogel matrix composition comprises: gelatin that is soluble in water at 50° C. and has an average molecular mass of about 75,000 Da to about 250,000 Da; and non-derivatized dextran having an average molecular mass of about 10,000 Da to about 1,000,000 Da;
    wherein the gelatin comprises about 60% by weight to about 95% by weight of the total weight of the combination of the gelatin and the non-derivatized dextran present in the hydrogel matrix composition;
    wherein the total concentration of the gelatin and the non-derivatized dextran in a hydrated form of the hydrogel matrix composition is about 50 mg/mL to about 400 mg/mL;
    wherein the hydrated form of the hydrogel matrix composition is phase-controllable so as to be a flowable, injectable liquid at a temperature of 35° C. and greater and is a solid or semi-solid gel matrix at lower temperatures; and
    wherein the hydrogel matrix composition is not covalently cross-linked before said applying and is not covalently cross-linked after said apply of the hydrogel matrix composition to the dermal or subdermal tissue.

2. The method of claim 1, further comprising closing the excision site with a closure selected from the group consisting of sutures, staples, glue, and combinations thereof.

3. The method of claim 1, wherein said applying comprises injecting the flowable, liquid matrix composition into the dermal or subdermal tissue around the excision site.

4. The method of claim 1, wherein the revision is effective such that recurrence of keloid formation or hypertrophic scarring at the excision site at 12 months post-treatment is 15% or less.

5. The method according to claim 1, wherein the gelatin has an average molecular mass of about 120,000 Da to about 180,000 Da.

6. The method according to claim 1, wherein the concentration of the gelatin and the non-derivatized dextran is about 100 mg/mL to about 300 mg/mL.

7. The method according to claim 1, wherein the flowable, injectable liquid has a flow rate of about 10 µL/s or greater when forced from a syringe through a ⅝ inch long 25 gauge needle under a syringe plunger pressure of 5 N at a temperature of 35° C. to 39° C.

8. The method according to claim 7, wherein the flowable, injectable liquid has a flow rate of about 10 µL/s to about 400 µL/s.

9. The method according to claim 3, wherein the injected composition has a residence time in the dermal or subdermal tissue of a mammal of about 3 days to about 60 days.

10. A method for reducing the external volume of a cutaneous keloid or hypertrophic scar, the method comprising:
    excising at least a portion of the keloid or hypertrophic scar tissue so as to form an excision site; and
    applying a hydrogel matrix composition to the dermal or subdermal tissue in or around the excision site;

wherein the hydrogel matrix composition comprises: gelatin that is soluble in water at 50° C. and has an average molecular mass of about 75,000 Da to about 250,000 Da; and non-derivatized dextran having an average molecular mass of about 10,000 Da to about 1,000,000 Da;

wherein the gelatin comprises about 60% by weight to about 95% by weight of the total weight of the combination of the gelatin and the non-derivatized dextran present in the hydrogel matrix composition;

wherein the total concentration of the gelatin and the non-derivatized dextran in a hydrated form of the hydrogel matrix composition is about 50 mg/mL to about 400 mg/mL;

wherein the hydrated form of the hydrogel matrix composition is phase-controllable so as to be a flowable, injectable liquid at a temperature of 35° C. and greater and is a solid or semi-solid gel matrix at lower temperatures;

wherein the hydrogel matrix composition is not covalently cross-linked before said applying and is not covalently cross-linked after said applying of the hydrogel matrix composition to the dermal or subdermal tissue; and wherein the external volume of any scar tissue present 12 months after said excision and application of the matrix composition relative to the external volume of the excised keloid or hypertrophic scar is about 15% or less.

11. The method of claim 10, wherein the hydrated form of the phase-controllable hydrogel matrix is a solid or semi-solid gel matrix at about average human skin temperature and below.

12. The method of claim 10, wherein said applying comprises injection through an 18 gauge to 27 gauge needle.

13. The method of claim 10, wherein the hydrated, flowable, injectable liquid form of the phase-controllable hydrogel matrix has a total solids content of about 0.5 g/mL or less.

14. The method of claim 1, wherein the hydrated form of the phase-controllable hydrogel matrix is a solid or semi-solid gel matrix at about average human skin temperature and below.

15. The method of claim 1, wherein the hydrated, flowable, injectable liquid form of the phase-controllable hydrogel matrix has a total solids content of about 0.5 g/mL or less.

16. The method of claim 3, comprising injecting the flowable, liquid matrix composition through an 18 gauge to 27 gauge needle.

17. A method for the revision of a cutaneous keloid or hypertrophic scar, the method comprising:
 excising at least a portion of the keloid or hypertrophic scar tissue so as to form an excision site; and
 applying a hydrogel matrix composition to the dermal or subdermal tissue in or around the excision site;
 wherein the hydrogel matrix composition comprises: gelatin that is soluble in water at 50° C. and has an average molecular mass of about 75,000 Da to about 250,000 Da; and non-derivatized dextran having an average molecular mass of about 10,000 Da to about 1,000,000 Da;
 wherein the gelatin comprises about 60% by weight to about 95% by weight of the total weight of the combination of the gelatin and the non-derivatized dextran present in the hydrogel matrix composition;
 wherein the total concentration of the gelatin and the non-derivatized dextran in a hydrated form of the hydrogel matrix composition is about 50 mg/mL to about 400 mg/mL;
 wherein the hydrogel matrix composition is configured to phase transition based on a temperature change from being a solid or semi-solid to being a flowable liquid and back, the hydrogel matrix composition being a flowable liquid hydrogel matrix at a temperature of 36° C. (+/−0.5° C.) and being a solid or semi-solid hydrogel matrix when at lower temperatures; and
 wherein the hydrogel matrix composition remains in the dermal or subdermal tissue of a mammal in the solid or semi-solid phase for a time of about 3 days to about 60 days before being degraded or bioabsorbed by the surrounding tissue.

* * * * *